(12) United States Patent
Wang et al.

(10) Patent No.: US 6,303,761 B1
(45) Date of Patent: Oct. 16, 2001

(54) TRIAMINEPENTAACETIC ACID COMPOUND AND PARAMAGNETIC METAL COMPLEX PREPARED FROM USING THE COMPOUND AS LIGAND

(75) Inventors: Yun-Ming Wang; Gin-Chung Liu, both of Kaohsiung; Chien-Hsun Lee, Ilan Hsien; Reu-Sheng Sheu, Tainan, all of (TW)

(73) Assignee: Department of Health The Executive Yuan, Republic of China, Taipei (TW)

( * ) Notice: Subject to any disclaimer, the term of this patent is extended or adjusted under 35 U.S.C. 154(b) by 0 days.

(21) Appl. No.: 09/489,410

(22) Filed: Jan. 21, 2000

(30) Foreign Application Priority Data

Apr. 23, 1999 (TW) .................................................. 88106510

(51) Int. Cl.⁷ ............................. C07F 5/00; C07F 11/00; C07C 229/00; A61B 5/055

(52) U.S. Cl. .................................... 534/15; 534/16; 556/1; 556/50; 556/63; 556/116; 556/148; 424/9.364; 562/565; 562/568

(58) Field of Search ................................. 556/1, 50, 148, 556/116, 63; 534/15, 16; 424/9.364; 562/565, 568

(56) References Cited

U.S. PATENT DOCUMENTS 4,933,441 * 6/1990 Gibby .................................... 536/112
5,707,605 * 1/1998 Meade et al. ........................ 424/9.35

* cited by examiner

Primary Examiner—Porfirio Nazario-Gonzalez
(74) Attorney, Agent, or Firm—Fish & Richardson P.C.

(57) ABSTRACT

The present invention provides a triaminepentaacetic acid compound which can be used as a ligand to coordinate to a metal ion to form a paramagnetic metal complex. The paramagnetic metal complex of the present invention can be used as a contrast agent for magnetic resonance imaging (MRI).

16 Claims, 12 Drawing Sheets

TRIAMINEPENTAACETIC ACID COMPOUND AND PARAMAGNETIC METAL COMPLEX PREPARED FROM USING THE COMPOUND AS LIGAND

BACKGROUND OF THE INVENTION

1. Field of the Invention

The present invention relates to a series of triaminepentaacetic acid compounds, and more particularly to a paramagnetic metal complex prepared from using the compound as the ligand, which can be used as a contrast agent for magnetic resonance imaging (MRI).

2. Description of the Prior Art

In recent years, magnetic resonance imaging (MRI) has developed rapidly and has become one of the most important techniques for diagnosing diseases. In order to increase sensitivity and accuracy, it is very important to develop a safe, stable, and targeting MRI contrast agent. Having a high magnetic moment, paramagnetic metal ions such as $Mn^{2+}$, $Fe^{3+}$, and $Gd^{+3}$ have potential to serve as MRI contrast agents. MRI contrast agents which have been approved by FDA of United States to be intravenously injected clinically include $Gd(DTPA)^{2-}$ (gadopentetate dimeglumine), $Gd(DOTA)^{-}$ (gadoterate megulumine), $Gd(DTPA-BMA)$ (bis-methylamide) (gadodiamide injection), $Gd(HP-DO3A)$ (gadoteridol), and MnDPDP (Teslascan). All of these five contrast agents belong to extracellular agents. $Gd(DTPA-BMA)$ and $Gd(HP-DO3A)$ are nonionic contrast agents, and $Gd(DTPA)^{2-}$, $Gd(DOTA)^{-}$, and MnDPDP are ionic ones. $Gd(DOTA)^{-}$ and $Gd(HP-DO3A)$ are macrocyclic, and MnDPDP, $Gd(DTPA)^{2-}$, and $Gd(DTPA-BMA)$ are open-chained.

Among the above cations, $Gd^{3+}$ has the greatest magnetic moment; thus, it has drawn the greatest interest. However, such a cation is not suitable for use alone as a MRI contrast agent due to the reasons of toxicity, pharmacokinetics, biodistribution, and effect. In addition, when $GdCl_3$ is intravenously injected to animal bodies, the $LD_{50}$ is very high, 0.3–0.5 mmol/kg [Weinmann et al. (1984) Am. J. Roentg., 142, 619]. Therefore, it is necessary to use an organic ligand to complex with $Gd^{3+}$ to form a stable metal complex to inhibit its toxicity and change the biodistribution and effect. Having a d orbital, $Mn^{2+}$ and $Fe^{3+}$ can form a stable complex with an organic ligand because of very strong partial covalent bonds [Lauffer et al. (1985) J. Comput. Assist. Tomogr., 9, 431]. It is more difficult for trivalent cations of lanthanide series to form complexes with organic ligands, since the f orbital belongs to the inner orbital which has less orientation and the interaction between the cation and the ligand is totally contributed by electrostatic interaction.

The toxicity of the metal complex can be derived from (1) free metal ion released from dissociation; (2) free organic ligand released from dissociation; and (3) the metal complex itself. In addition, metabolites may be even more toxic than the metal complex itself. Since metal ions and organic ligands may form bonding with proteins, enzymes, or cell membrane in tissues by electrostatic interaction, hydrogen bonds, or covalent bonds, they have higher toxicity than the metal complex itself for animal bodies.

The toxicity of the metal ion is derived from coordination of ions to oxygen, nitrogen, or sulfur atom of macromolecules in animal bodies, thus changing the dynamic equilibria necessary to sustain life. For example, $Gd^{3+}$ easily replaces $Ca^{2+}$ and binds to $Ca^{2+}$ binding sites to complex with the above atoms. The toxicity of the organic ligand is due to the effect to the tissues by the ligand itself. The toxicity of the metal complex may be derived from various reasons. For example, when a large dose of the metal complex is injected, it will cause a difference in osmolality between intracellular and extracellular compartments. Water is drawn out of cells as a result of the osmotic gradient, causing cellular and circulatory damage. Other toxicity reasons include enzyme inhibition or alternation of membrane functions.

To design a new contrast agent for MRI, the stability of the metal complex is the main concern. The contrast agent should be effective during the period of time from injecting it to the body to excreting it from the body. Therefore, stability is required for this residence time. Three factors should be considered to determine the stability of a gadolinium complex in vivo; that is, thermodynamic stability constant, conditional stability constant, and selectivity constant [Cacheris et al. (1990) Magn. Reson. Imag., 8, 467].

Recent reseach on MRI contrast agents can be classified in two categories and are described as follows:

(1) Ionic MRI contrast agents: Such contrast agents include $[Gd(DTPA)]^{2-}$, $[Gd(EOB-DTPA)]^{2-}$ [ethoxybenzyl diethylene triaminepentaacetate-gadolinium(III)], $[Gd(BOPTA)]^{2-}$ [benzyloxypropionic tetraacetate-gadolinium (III)], and $[Gd(DOTA)]^{-1}$. The thermodynamic stability constants of $[Gd(DTPA)]^{2-}$, $[Gd(BOPTA)]^{2-}$ and $[Gd(DOTA)]^{-1}$ are $10^{22.46}$, $10^{22.0}$, and $10^{25.3}$ [Vittadin et al. (1988) Invest. Radiol., 23, 246; and Pavone et al. (1990) Radiology, 176, 61]. Since these gadolinium complexes are ionic, counter ions, generally meglumine, should be added to form ion pair for storage. However, this will increase the osmotic pressure of the solution.

(2) Non-ionic MRI contrast agents: Such contrast agents have a lower osmotic pressure than ionic contrast agents. Thus, non-ionic MRI contrast agents can be injected in a larger dose in order to achieve higher enhancement effect. Non-ionic MRI contrast agents includes [Gd(DTPA-BMA)] [diethylenetriamine pentaacetic acid bis(methylamide)-gadolinium(III)], [Gd(DTPA-BP)] [N,N-bis(2-pyridylmethyl)diethylenetriamine-N,N',N"-triacetate-gadolinium(III)], [Gd(HP-DO3A)] [10-(2-hydroxypropyl)-1,4,7,10-tetraaza-cyclododecane-1,4,7-triacetate-gadolinium(III)], and [Gd(DO3A)] [1,4,7,10-tetraazacyclododecane-1,4,7-triacetate-gadolinium(III)]. These non-ionic gadolinium complexes have a lower thermodynamic stability than ionic gadolinium complexes. For example, the thermodynamic stability constants of [Gd(DTPA-BMA)], [Gd(DTPA-BP], [Gd(HP-DO3A)] and [Gd(DO3A)] are $10^{16.85}$, $10^{16.83}$, and $10^{23.8}$ and $10^{21.0}$ [Kumar et al. (1994) Inorg. Chem., 33, 3567; and Brucher et al. (1991) Inorg. Chem., 30, 2092]. However, these non-ionic gadolinium complexes are very stable under the physiological conditions of bodies.

The toxicity of the open-chained gadolinium complex, no matter ionic or non-ionic, is mainly related to selectivity constant. For example, the selectivity constant is in the order of [Gd(DTPA-BMA)] ($10^{9.04}$)>[Gd(DTPA)]$^{2-}$ ($10^{7.04}$)>[Gd(DTPA-BP]) ($10^{5.32}$), which is consistent to the order of $LD_{50}$, [Gd(DTPA-BMA)] (14.8 mmol/kg)>[Gd(DTPA)]$^{2-}$ (5.6 mmol/kg)>[Gd(DTPA-BP]) (3.2 mmol/kg).

The relaxivity of the metal complex is also an important consideration for designing an MRI contrast agent. When the denticity of the organic ligand increases, the coordinated water molecules in the inner sphere of the metal complex decreas, thus decreasing the relaxation effect. Taking [Gd(EDTA)]$^-$ for an example, EDTA has 6 denticities and $Gd^{3+}$ has 8–9 binding sites, thus, 2–3 inner sphere water molecules will be present in [Gd(EDTA)]⁻, and the relaxivity ($R_1$) is as high as 6.3 $(mM\ s)^{-1}$. DTPA, EOB-DTPA, BOPTA, DOTA, HP-DO3A and DTPA-BMA have 8 denticities, thus, only 1 inner sphere water molecule will be present in their gadolinium complex, and the relaxivities are 3.7, 5.3, 5.65, 5.8, 3.7, and 5.1 $(mM\ s)^{-1}$ respectively. Gd(III)-TREN-Me-3,2-HOPO [tris(3-hydroxy-1-methyl-2-oxo-1,1-didehydro-pyridine-4-carboxamido)ethylamine] has 2 inner sphere water 7 molecules, and the relaxivity is increased to 10.5 $(mM\ s)^{-1}$ (37° C., 20 MHz) [Xu et al. (1995) J. Am. Chem. Soc., 117, 7245]. Petre et al. modifies DTPA by introducing p-butylbenzyl with higher lipid solubility to the ethyl group of DTPA to form Gd(1RS)-1-(p-butylbenzyl)-DTPA, so as to make the contrast agent absorbed by livers [Petre et al. (1995) Magn. Reson. Med., 35, 532]. Also, Runge et al. synthesizes 2,5-BPA-DO3A and $Cy_2DOTA$ (biscyclohexyl-DOTA) to increase their lipid solubility [Runge et al. (1996) Invest. Radiol., 31, 11]. Lammers et al. synthesizes N,N"-bis[N-(d-gluco-2,3,4,5,6-pentahydroxyhexyl)carbamoylmethyl]diethylenetriamine-N,N',N"-triacetic acid (DTPA-BGLUCA) and N,N"-bis[N-(3-aza-D-galacto-5,6,7,8,9-pentahydroxynonyl) carbamoylmethyl]diethylenetriamine-N,N',N"-triacetic acid (DTPA-BENGALAA). The purpose of introducing various aminoglucoses is to increase the functional group, so as to increase the outer sphere water molecules, thus increasing relaxivity [Lammers et al. (1997) Inorg. Chem., 36, 2527]. Vauthey et al. synthesizes 2,11-dihydroxy-4,9-dioxa-1,12-bis[1,4,7,10-tetraaza-4,7,10-tris(carboxymethyl) cyclododecyl]dodecane-gadolinium(III)) {BO[Gd(DO3A) $(H_2O)]2$} dimer. Since the dimer has two inner sphere water molecules (q=2), and the rotational time ($\tau_r$) of the dimer increases twice compared with the monomer, therefore, the relaxivity ($R_1$) increases from 3.4 (monomer) to 4.61 $dm^3\ mmol^{-1}\ s^{-1}$ (dimer) [Vauthey et al. (1996) Inorg. Chem., 35, 3375]. Schumann et al. synthesizes 1,4,7,10,13,16,19,22-octaazacyclotetracosane-1,4,7,10,13,16,19,22-octaacetic acid ($H_8OTEC$) and 1,4,7,10,14,17,20,23-octaazacyclohexacosane-1,4,7,10,14,17,20,23-octaacetic acid ($H_8HEC$). The two ligands have 16 coordinating sites and can form a bimetallic complex with lanthanide series metal ion, which have higher water solubility [Schumann et al. (1997) J. Chem. Ber./Recueil, 130, 267]. Aime et al synthesize 3,6,9,15-tetraazabicyclo[9.3.1]pentadeca-1(15), 11,13-triene-3,6,9-triacetic acid (PCTA-[12]), 3,6,10,16-tetraazabicyclo[10.3.1]-hexadeca-1(16),12,14-triene-3,6, 10-triacetic acid (PCTA-[13]), and 3,7,11,17-tetraazabicyclo [11.3.1]heptadeca-1(17),13,15-triene-3,7,11-triacetic acid (PCTA-[14]), all of which contains pyridine and seven coordinating sites [Aime et al. (1997) Inorg. Chem., 36, 2992]. The complex of pyridine-containing ligands and gadolinium ions has two inner sphere water molecules. The relaxivities of PCTA[12], PCTA[13], PCTA[14] are 6.9, 6.3, and 5.9 $dm^3\ mmol^{-1}\ s^{-1}$ respectively, which are much higher than that of [Gd(DOTA)] (3.56 $dm^3\ mmol^{-1}\ s^{-1}$) containing one inner sphere water molecule. The stability constants of PCTA[12]-Gd(III) and PCTA[13]-Gd(III) are 20.8 and 19.3 respectively, which are higher than that of [Gd(DTPA-BMA)] (16.85) and lower than those of $[Gd(DTPA)]^{2-}$ (22.4) and [Gd(DOTA)]⁻ (24.6).

There is still a need to develop a better MRI contrast agent.

SUMMARY OF THE INVENTION

Therefore, an object of the present invention is to provide an ionic metal complex which is stable and suitable for use as a contrast agent for magnetic resonance imaging (MRI).

To achieve the above object, the present invention provides a ligand which is a triaminepentaacetic acid compound represented by the following formula

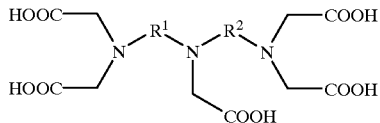

wherein
$R^1$ is —$(CH_2)_n$— or —$(CH_2)_n$—X—$(CH_2)_n$—, wherein n=1 to 5, X is —O— or —S—;
$R^2$ is —$(CH_2)_m$— or —$(CH_2)_m$—X—$(CH_2)_m$—, wherein m=1 to 5, X is —O— or —S—; and
$R^1$ and $R^2$ can be the same or different.

The present invention also provides a paramagnetic metal complex represented by the formula ML, which can be used as a contrast agent for magentic resonance imaging, wherein M is a central metal ion, which is selected from the group consisting of ions of metals of Lanthanide series, manganese ion, iron ion, cobalt ion, copper ion, nickel ion, and chromium ion; and L is an organic ligand which includes a compound represented by the following formula

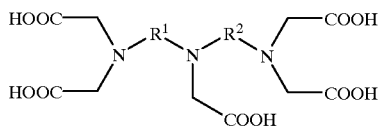

wherein
$R^1$ is —$(CH_2)_n$— or —$(CH_2)_n$—X—$(CH_2)_n$—, wherein n=1 to 5, X is —O— or —S—;
$R^2$ is —$(CH_2)_m$— or —$(CH_2)_m$—X—$(CH_2)_m$—, wherein m=1 to 5, X is —O— or —S—; and
$R^1$ and $R^2$ can be the same or different.

DETAILED DESCRIPTION OF THE INVENTION

Figure 1:
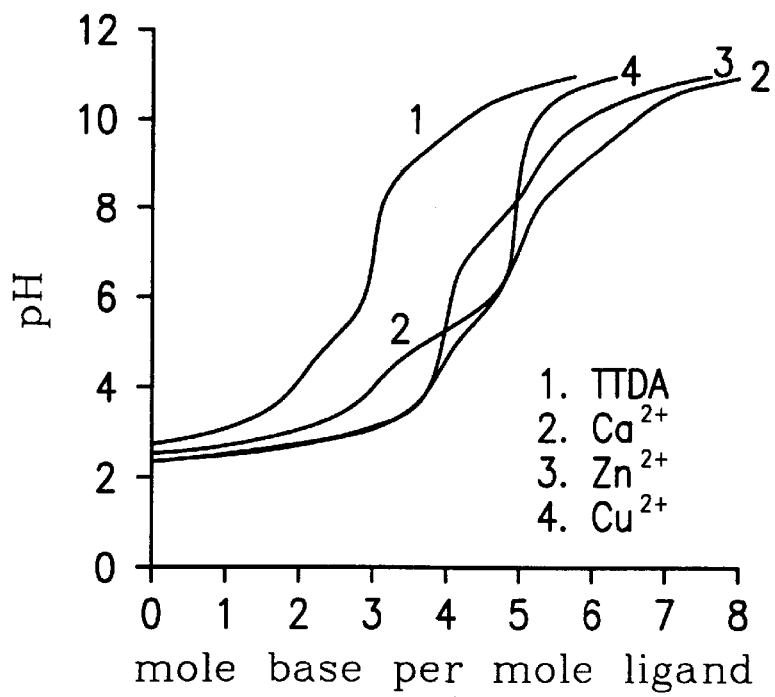
FIG. 1 shows the titration curves of (1) TTDA and the metal complexes of TTDA with various metal ions (2) $Ca^{2+}$, (3) $Zn^{2+}$, and (4) $Cu^{2+}$ in 1:1 molar ratio at 25±0.1° C., I=0.1 mol $dm^{-3}$ ($MeNNO_3$).

The triaminepentaacetic acid compound of the present invention is represented by the following formula

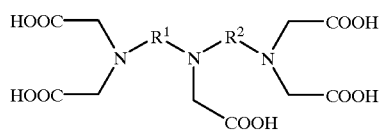

(I)

wherein

R$^1$ is —(CH$_2$)$_n$— or —(CH$_2$)$_n$—X—(CH$_2$)$_n$—, wherein n=1 to 5, X is —O— or —S—;

R$^2$ is —(CH$_2$)$_m$— or —(CH$_2$)$_m$—X—(CH$_2$)$_m$—, wherein m=1 to 5, X is —O— or —S—; and R$^1$ and R$^2$ can be the same or different.

According to a preferred embodiment of the present invention, in formula (I), R$^1$ is —(CH$_2$)$_n$—X—(CH$_2$)$_n$—, wherein n=2 to 4, X is —O— or —S—; and R$^2$ is —(CH$_2$)$_m$—X—(CH$_2$)$_m$—, wherein m=2 to 4, X is —O— or —S—.

According to a second preferred embodiment of the present invention, in formula (I), R$^1$ is —(CH$_2$)$_n$—, wherein n=2 to 4; and R$^2$ is —(CH$_2$)$_m$—X—(CH$_2$)$_m$—, wherein m=2 to 4, X is —O— or —S—.

According to a third preferred embodiment of the present invention, in formula (I), R$^1$ is —(CH$_2$)$_n$—X—(CH$_2$)$_n$—, wherein n=2 to 4, X is —O— or —S—; and R$^2$ is —(CH$_2$)$_m$—, wherein m=2 to 4.

According to a fourth preferred embodiment of the present invention, in formula (I), R$^1$ is —(CH$_2$)$_n$—, wherein n=2 to 4; and R$^2$ is —(CH$_2$)$_m$—, wherein m=2 to 4. Representative examples of the triaminepentaacetic acid according to this embodiment include TTDA (n=2, m=3) [3,6,10-tri(carboxymethyl)-3,6,10-triazadodecanedioic acid], TTRA (n=3, m=3) [3,7,11-tri(carboxymethyl)-3,7,11-triazatridecanedioic acid], and TTEA (n=3, m=4) [3,7,12-tri(carboxymethyl)-3,7,12-triazatetradecanedioic acid].

The triaminepentaacetic acid compound of the present invention can be used as a ligand to coordinate to a metal ion to form a paramagnetic metal complex represented by the formula ML. M is a central metal ion, which is selected from the group consisting of ions of metals of Lanthanide series, manganese ion, iron ion, cobalt ion, copper ion, nickel ion, and chromium ion. Examples are Gd(+3), Fe(+3), and Mn(+3). L is the triaminepentaacetic acid compound of formula (I) as mentioned above. The paramagnetic metal complex of the present invention can be used as a contrast agent for magnetic resonance imaging (MRI).

The following examples are intended to illustrate the process and the advantages of the present invention more fully without limiting its scope, since numerous modifications and variations will be apparent to those skilled in the art.

EXAMPLES

The synthesis of the DTPA derivatives is depicted as follows:

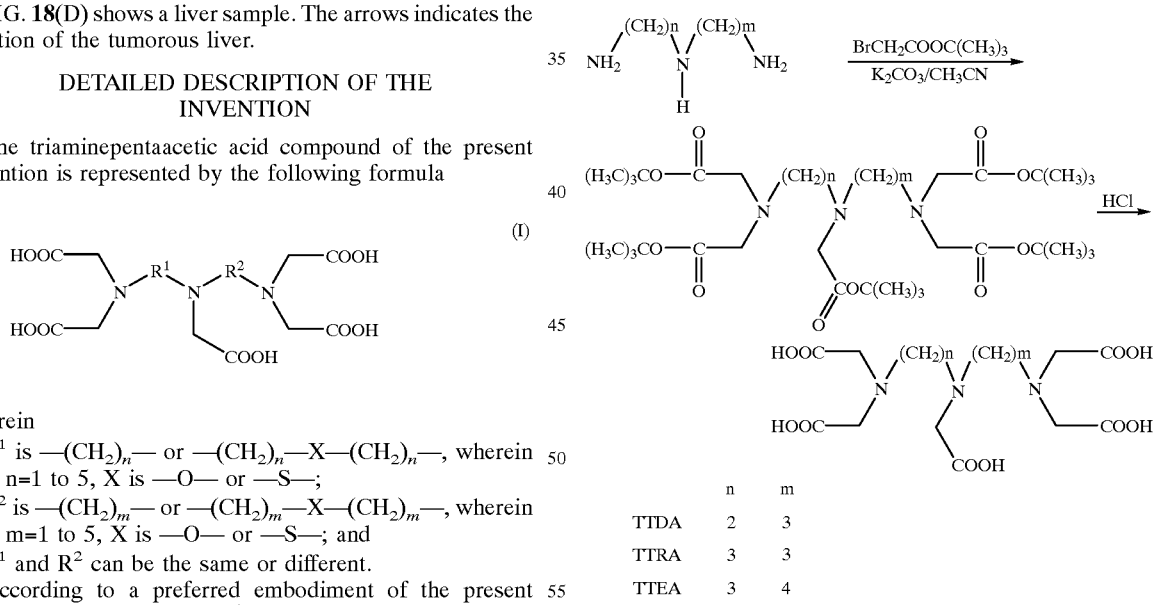

|      | n | m |
|------|---|---|
| TTDA | 2 | 3 |
| TTRA | 3 | 3 |
| TTEA | 3 | 4 |

Example 1

Preparation of TTDA [3,6,10-tri(carboxymethyl)-3,6,10-triazadodecanedioic acid]

3.0 g (25.64 mmol) of N-(2-aminoethyl)-1,3-propanediamine and 18.41 g (133 mmol) of anhydrous potassium carbonate in 150 ml of $CH_3CN$ (acetonitrile) were stirred thoroughly. Then, 25.56 g (136.19 mmol) of tert-butyl bromoacetate was slowly added and the mixture was stirred for 24 hours. Removal of the solvent at reduced pressure on a rotary evaporator gave a residue which was partitioned between 100 ml of water and 100 ml of chloroform. The aqueous layer was separated and then extracted with two 100 ml portions of chloroform. The chloroform portions were combined and dried over $MgSO_4$. Filtration and evaporation of solvent gave an amber oil, which was purified by chromatography on silica gel using ethyl acetate/n-hexane (1:4, v/v) as the eluent to give a gold oil. The oil was then acidified with 25 ml of concentrated aqueous hydrochloric acid (12 mol $dm^{-3}$). The acid was removed by rotary evaporation and the residue taken up in water (20 ml). The solution was loaded onto an AG 50W×8 cation exchange resin column (200–400 mesh, $H^+$ form, 3.5×20 cm) and washed with distilled water (1000 ml). The crude product was eluted with 0.5 mol $dm^{-3}$ $NH_3$(aq). The solution was concentrated by rotary evaporation and the white residue applied to an AG1×8 anion exchange resin column (200–400 mesh, $HCO_2H$ form, 3.5×20 cm). The column was washed with distilled water and eluted with 0.5 mol $dm^{-3}$ formic acid. The eluate was concentrated by rotary evaporation for 12 hours to give a white solid. Yield: 6.58 g (58%). $^1$H-NMR ($D_2O$, pD 2.9): 3.83 (s, 8H, terminal, $NCH_2COOH$), 3.80 (s, 2H, central, $NCH_2COOH$), 3.51 (s, 4H, $NCH_2CH_2N$), 2.28 (t, 4H, $NCH_2CH_2CH_2N$), 2.16 (m, 2H, $NCH_2CH_2CH_2N$). $^{13}$C-NMR ($D_2O$): δ 176.52, 175.01, 173.45, 60.46, 60.23, 58.76, 56.37, 55.03, 54.41, 53.56, 23.04. Anal. Calcd (found) for $C_{15}N_{25}N_3O_{10}$ $2H_2O$: C, 40.63 (40.61); H, 6.59 (6.74); N, 9.47 (9.31).

Example 2

Preparation of TTRA [3,7,11-tri(carboxymethyl)-3,7,11-triazatridecanedioic acid]

2.0 g (15.24 mmol) of N-(3-aminopropyl)-1,3-propanediamine and 10.5 g (76 mmol) of anhydrous potassium carbonate in 150 ml of $CH_3CN$ (acetonitrile) were stirred thoroughly. Then, 15.46 g (79.25 mmol) of tert-butyl bromoacetate was slowly added and the mixture was stirred for 24 hours. Removal of the solvent at reduced pressure on a rotary evaporator gave a residue which was partitioned between 100 ml of water and 100 ml of chloroform. The aqueous layer was separated and then extracted with two 100 ml portions of chloroform. The chloroform portions were combined and dried over $MgSO_4$. Filtration and evaporation of solvent gave an amber oil, which was purified by chromatography on silica gel using ethyl acetate/methanol as the eluent to give a gold oil. The oil was then acidified with 25 ml of concentrated aqueous hydrochloric acid (12 mol $dm^{-3}$) The acid was removed by rotary evaporation and the residue taken up in water (20 ml). The solution was loaded onto an AG 50W×8 cation exchange resin column (200–400 mesh, $H^+$ form, 3.5×20 cm) and washed with distilled water (1000 ml). The crude product was eluted with 0.5 mol $dm^{-3}$ $NH_3$(aq). The solution was concentrated by rotary evaporation and the white residue applied to an AG1×8 anion exchange resin column (200–400 mesh, $HCO_2H$ form, 3.5×20 cm). The column was washed with distilled water and eluted with 0.5 mol $dm^{-3}$ formic acid. The eluate was concentrated by rotary evaporation for 12 hours to give a white solid. Yield: 4.74 g (68%). $^1$H-NMR ($D_2O$, pD 3.51): 3.82 (s, 8H, terminal, $NCH_2COOH$), 3.76 (s, 2H, central, $NCH_2COOH$), 3.32 (m, 8H, $NCH_2CH_2CH_2N$), 2.16 (m, 4H, $NCH_2CH_2CH_2N$). $^{13}$C-NMR ($D_2O$): δ 174.78, 173.82, 60.28, 58.82, 56.13, 54.72, 22.68. Anal. Calcd (found) for $C_{16}N_{27}N_3O_{10}$ $2H_2O$: C, 42.01 (41.80); H, 6.83 (6.98); N, 9.18 (9.09).

Example 3

Preparation of TTEA [3,7,12-tri(carboxymethyl)-3,7,12-triazatetradecanedioic acid]

2.0 g (13.77 mmol) of N-(3-aminopropyl)-1,4-butanediamine and 9.52 g (68.85 mmol) of anhydrous potassium carbonate in 150 ml of $CH_3CN$ (acetonitrile) were stirred thoroughly. Then, 13.97 g (71.60 mmol) of tert-butyl bromoacetate was slowly added and the mixture was stirred for 24 hours. Removal of the solvent at reduced pressure on a rotary evaporator gave a residue which was partitioned between 100 ml of water and 100 ml of chloroform. The aqueous layer was separated and then extracted with two 100 ml portions of chloroform. The chloroform portions were combined and dried over $MgSO_4$. Filtration and evaporation of solvent gave an amber oil, which was purified by chromatography on silica gel using ethyl acetate/methanol as the eluent to give a gold oil. The oil was then acidified with 20 ml of concentrated aqueous hydrochloric acid (12 mol $dm^{-3}$). The acid was removed by rotary evaporation and the residue taken up in water (20 ml). The solution was loaded onto an AG 50W×8 cation exchange resin column (200–400 mesh, $H^+$ form, 3.5×20 cm) and washed with distilled water (1000 ml). The crude product was eluted with 0.5 mol $dm^{-3}$ $NH_3$(aq). The solution was concentrated by rotary evaporation and the white residue applied to an AG1×8 anion exchange resin column (200–400 mesh, $HCO_2H$ form, 3.5×20 cm). The column was washed with distilled water and eluted with 0.5 mol $dm^{-3}$ formic acid. The eluate was concentrated by rotary evaporation for 12 hours to give a white solid. Yield: 4.85 g (72%). $^1$H-NMR ($D_2O$, pD 3.43): 3.83 (s, 4H, terminal, $NCH_2COOH$), 3.80 (s, 4H, central, $NCH_2COOH$), 3.76 (s, 2H, $NCH_2COOH$), 3.26–3.78 (m, 8H, $NCH_2$), 2.17 (t, 2H, $NCH_2CH_2N$), 1.78 (m, 4H, $NCH_2CH_2CH_2CH_2N$). $^{13}$C-NMR ($D_2O$): δ 173.77, 173.53, 173.47, 60.35, 58.79, 58.22, 56.99, 55.81, 54.58, 23.99, 23.59, 22.60. Anal. Calcd (found) for $C_{17}N_{29}N_3O_{10}$ $3H_2O$: C, 41.72 (41.77); H, 7.21 (7.55); N, 8.58 (8.75).

Example 4

Preparation of $[Gd(TTDA)]^{2-}.7H_2O$ 1.5 g (3.38 mmol) of $TTDA.2H_2O$ obtained from example 1, 0.59 g (1.65 mmol) of gadolinium chloride, and 15 ml of deionized water were mixed and reluxed for 24 hours. After reaction is completed, 10 ml of methanol was slowly added and colorless crystals were formed. Yield: 1.47 g (63%). Anal. Calcd (found) for $C_{15}H_{25}N_3O_{10}$ $7H_2O$: C, 26.07 (26.01); H, 4.96 (4.85); N, 6.08 (5.92).

Discussion on Thermodynamic Constants

1. Protonation Constants:

Potentiometric titrations were performed with an automatic titrator system to determine the protonation constants of the organic ligands and the stability constants of the metal complexes. The autotitrating system consists of a 702 SM Titroprocessor, a 728 stirrer, and a PT-100 combination pH electrode (Metrohm). The pH electrode was calibrated using two standard buffer solutions with pH 7.0±0.05 and pH 4.0±0.05 respectively. The ionic strength was 0.10 mol $dm^{-3}$ $Me_4NNO_3$ $((CH_3)_4NNO_3)$. The ligands used in this experiment should have high purity. If the important functional groups of the ligand have not been protonated, suitable acid should be added to make it protonated before titration. The titrant used was 0.1 mol $dm^{-3}$ NaOH with a titration amount of 0.005 ml/time.

The protonation constants of the ligand were calculated using a FORTRAN computer program PKAS. The overall stability constants of the various metal complexes formed in aqueous solution were determined from the titration data with the FORTRAN computer program BEST. The average difference between observed and calculated $-\log[H^+]$ was <0.04 throughout all titrations. The species distribution diagrams were calculated with the FORTRAN programs SPE and SPEPLOT.

The potentiometric titration curves of the organic ligands TTDA, TTRA, and TTEA are shown in FIG. 1 to FIG. 4. The protonation constants of the organic ligands is calculated using the FORTRAN computer program PKAS and are shown in Table 1. From FIG. 1, it is shown that there are two buffering regions (pH 2.5–5.5 and pH 6–9) in the TTDA titration curve. When the number of mole base per mole ligand (value a) is equal to 2, the curve is rising steeply. This is due to the large difference between the third ($\log K_3^H = 5.12$) and fourth protonation constant ($\log K_4^H = 2.8$) of TTDA. When a=3, the curve is rising steeply again, which is due to the large difference between the second ($\log K_2^H = 8.92$) and third protonation constant ($\log K_3^H = 5.12$) of TTDA. The difference between the first ($\log K_1^H = 10.60$) and second protonation constant ($\log K_2^H = 8.92$) is not obvious.

Figure 3:
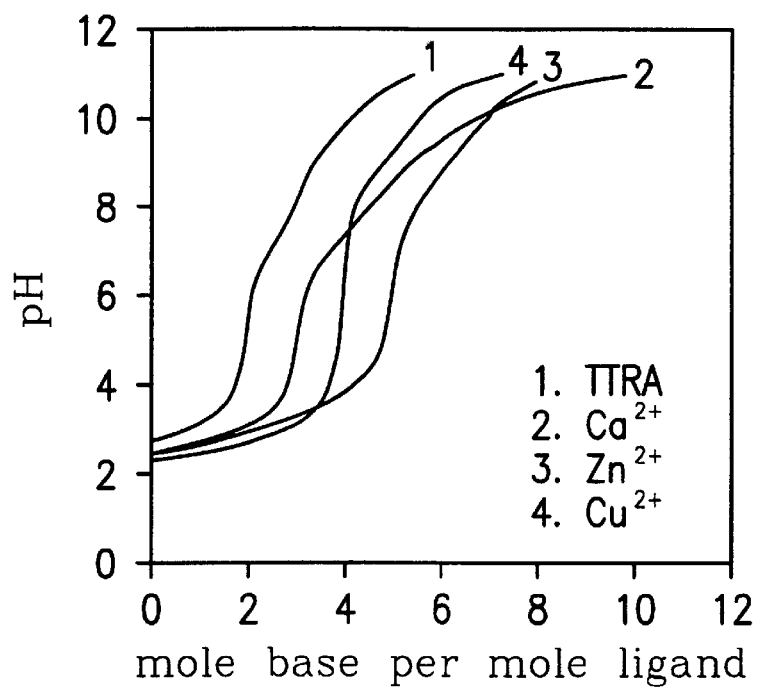
FIG. 3 shows the titration curves of (1) TTRA and the metal complexes of TTRA with various metal ions (2) $Ca^{2+}$, (3) $Zn^{2+}$, and (4) $Cu^{2+}$ in 1:1 molar ratio at 25±0.1° C., I=0.1 mol $dm^{-3}$ ($MeNNO_3$).

From FIG. 3, it is shown that there are two buffering regions (pH 3–8 and pH 8–10) in the TTRA titration curve. When a=2, the curve is rising steeply. This is due to the large difference between the third ($\log K_3^H = 7.00$) and fourth protonation constant ($\log K_4^H = 3.10$) of TTRA. When a=3, the curve is rising steeply again, which is due to the large difference between the second ($\log K_2^H = 9.12$) and third protonation constant ($\log K_3^H = 7.00$).

Figure 4:
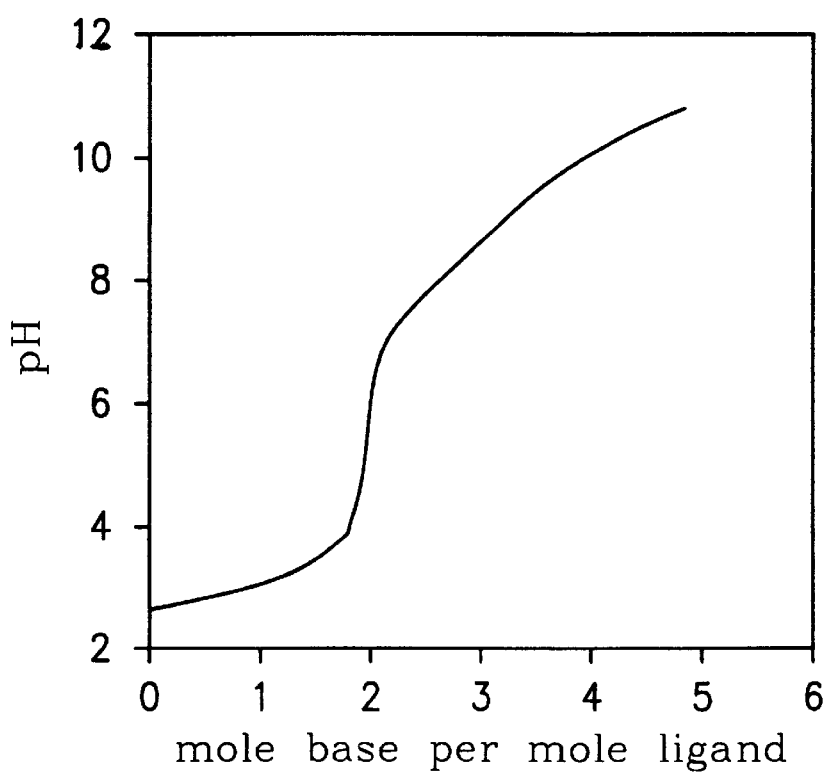
FIG. 4 shows the titration curve of TTEA at 25±0.1° C., I=0.1 mol $dm^{-3}$ ($MeNNO_3$).

From FIG. 4, it is shown that there are two buffering regions (pH 2.8–8 and pH 8–10) in the TTEA titration curve. When a=2, the curve is rising steeply. This is due to the large difference between the third ($\log K_3^H = 7.71$) and fourth protonation constant ($\log K_4^H = 3.04$) of TTEA. When a=3, the curve is rising steeply again, which is due to the large difference between the second ($\log K_2^H = 9.46$) and third protonation constant ($\log K_3^H = 7.71$).

In the titration curve, the steep rising curve indicates that the two protonation constants differ greatly, and the smooth rising curve indicates that the two protonation constants differ little.

TABLE 1

The protonation constants of the organic ligands TTDA, TTRA, TTEA, DTPA-BMA, and DTPA at 25.0 ± 0.1° C. in aqueous Me$_4$NNO$_3$ (I = 0.10 mol dm$^{-3}$)

| | log K$_n^H$ | | | | |
|---|---|---|---|---|---|
| Equilibrium | TTDA | TTRA | TTEA | DTPA-BMA | DTPA |
| [HL]/[L][H] | 10.60(2) | 10.63(3) | 10.69(0) | 9.51(2) | 10.49 |
| [H$_2$L]/[HL][H] | 8.92(2) | 9.12(2) | 9.46(3) | 4.49(1) | 8.60 |
| [H$_3$L]/[H$_2$L][H] | 5.12(2) | 7.00(3) | 7.71(2) | 3.53(1) | 4.28 |
| [H$_4$L]/[H$_3$L][H] | 2.80(9) | 3.10(5) | 3.04(5) | | 2.64 |
| Σ PK$_a$ | 27.44 | 29.85 | 30.90 | 17.53 | 26.01 |

DTPA-BMA = diethylenetriamine pentaacetic acid bis(methylamide)-gadolinium(III)
DTPA = diethylenetriaminepentaacetic acid From Table 1, it can be seen that the basicity ($\Sigma pK_a$) of TTDA, TTRA, and TTEA is 27.44, 29.85, and 30.90 respectively, which increases by 1.43, 3.84, and 4.89 compared with the basicity ($\Sigma pK_a = 26.01$) of DTPA. This indicates that when the carbon number between amino groups increases, the basicity increases. The first protonation constants of TTDA, TTRA, and TTEA are very close, and the second protonation constants are very close too. The third protonation constant decreases in the order TTEA ($\log K_3^H = 7.71$) > TTRA ($\log K_3^H = 7.00$) > TTDA ($\log K_3^H = 5.12$) > DPTA ($\log K_3^H = 4.28$) This can be explained by considering the chain length (carbon number) between the amino groups. In general, the protonation constant increases with the chain length between the amino groups.

2. Thermodynamic Stability Constants:

The complexes of Zn$^{2+}$, Ca$^{2+}$, Cu$^{2+}$, and Gd$^{3+}$ with ligands TTDA, TTRA, and TTEA may have a stability constant higher than 10. Therefore, the stability constant is determined using the following two methods:

(1) Direct Potentiometric Titration: The metal ion and ligand is mixed in 1:1 molar ratio. NaOH is used as the titrant with 0.005 ml/time to titrate the mixed solution. The stability constant of the metal complex is calculated from the titration data by the program BEST.

(2) Ligand-ligand Competition Titration: The metal ion, ligand, and EDTA is mixed in 1:1:1 molar ratio. NaOH is used as the titrant with 0.005 ml/time to titrate the mixed solution. The titration interval is 10–15 minutes to ensure the equilibrium of the competition reaction. The stability constant of the metal complex is calculated from the titration data by the program BEST.

Figure 2:
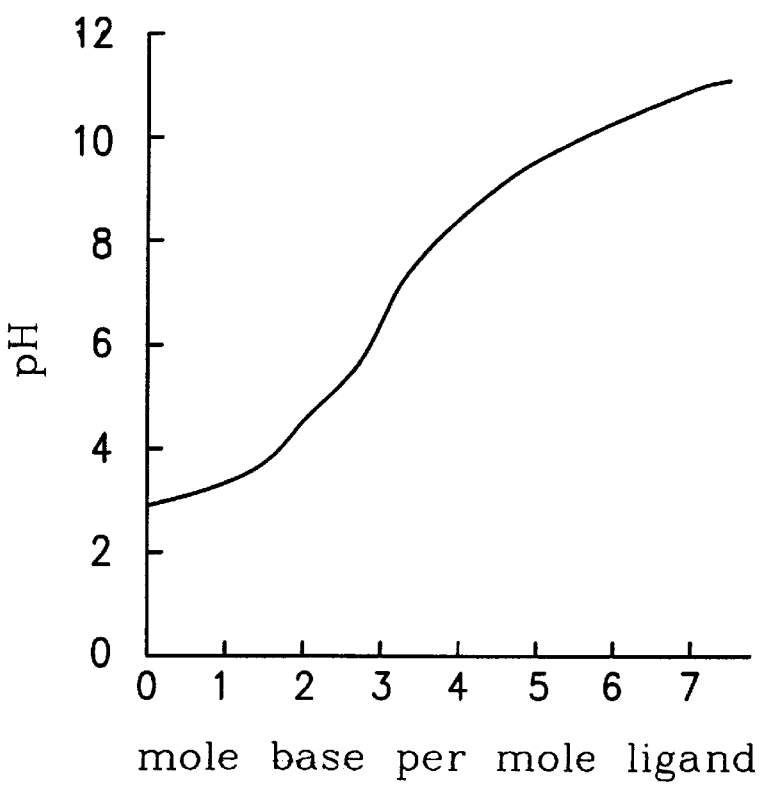
FIG. 2 shows the titration curve of TTDA/EDTA/$Gd^{3+}$ in 1:1:1 molar ratio at 25±0.1° C., I=0.1 mol $dm^{-3}$ ($MeNNO_3$).

From the direct potentiometric titration, the titration curves of the TTDA, TTRA, and TTEA with metal ions Ca$^{2+}$, Zn$^{2+}$, and Cu$^{2+}$ are shown in FIGS. 1–3. Referring to FIG. 1, it can be seen that the Ca$^{2+}$-TTDA (molar ratio 1:1) complex has very similar pH value to the single TTDA solution. This indicates that in the beginning, Ca$^{2+}$ does not immediately coordinate with the unprotonated or protonated organic ligand to form metal complex. As to Zn$^{2+}$ and Cu$^{2+}$ metal ions, they bind with TTDA ligand in the beginning; therefore, the pH value is lower than that of the single TTDA solution. The potentiometric curves of TTDA with Ca$^{2+}$, Zn$^{2+}$, and Cu$^{2+}$ rise rapidly in the pH 3.5–10 range. The inflection point is at a=4 and a=5, indicating that the complex is present in the form of [MHL]$^{2-}$ at a=4, and five protons are dissociated at a=5.

Referring to FIG. 3, the potentiometric curve of TTRA-Ca$^{2+}$ rises rapidly in the pH 3–6.5 range and those of TTRA with Zn$^{2+}$ and Cu$^{2+}$ rise rapidly in the pH 3.5–9 range. The inflection points of the metal complexes of TTRA with Ca$^{2+}$, Zn$^{2+}$ and Cu$^{2+}$ are a=3, 4, and 5 respectively, indicating that different metal complexes have different proton numbers dissociated.

The thermodynamic constants determined by the program BEST are shown in Table 2. The stability constants of TTDA with Gd$^{3+}$, Ca$^{2+}$, Zn$^{2+}$, and Cu$^{2+}$ are in the order [Gd (TTDA)]$^{2-}$ (22.77)>[Cu(TTDA)]$^{3-}$ (19.31)>[Zn(TTDA)]$^{3-}$ (18.59)>[Ca(TTDA)]$^{3-}$ (14.45). For Ca$^{2+}$, TTDA complex has a greater stability constant than DTPA complex. For Zn$^{2+}$ and Cu$^{2+}$, TTDA complex has a smaller stability constant than DTPA complex. For Gd$^{3+}$, TTDA complex has a similar stability constant to DTPA complex, [Gd(TTDA)]$^{2-}$ (22.77)=[Gd(DTPA)]$^{2-}$ (22.46).

TABLE 2

Thermodynamic constants of the of Gd$^{3+}$, Zn$^{2+}$, Ca$^{2+}$, and Cu$^{2+}$ complexes of organic ligands TTDA, TTRA, TTEA, DTPA-BMA, and DTPA at 25.0 ± 0.1° C. in aqueous Me$_4$NNO$_3$ (I = 0.10 mol dm$^{-3}$)

| | log K | | | | |
|---|---|---|---|---|---|
| Parameter | TTDA | TTRA | TTEA | DTPA-BMA | DTPA |
| [GdL]/[Gd][L] | 22.77 | 15.89 | — | 16.95 | 22.46 |
| [GdHL]/[GdL][H] | — | 5.95 | — | — | |
| log K$_{GdL'}$(pH 7.4) | 18.04 | 10.93 | — | 14.84 | 18.14 |
| [CaL]/[Ca][L] | 14.45 | 13.52 | 13.48 | 7.72 | 10.75 |
| [CaHL]/[CaL][H] | 6.06 | 8.02 | 8.2 | 5.11 | 6.11 |

TABLE 2-continued

Thermodynamic constants
of the of $Gd^{3+}$, $Zn^{2+}$, $Ca^{2+}$, and $Cu^{2+}$ complexes of
organic ligands TTDA, TTRA, TTEA, DTPA-BMA,
and DTPA at 25.0 ± 0.1° C. in
aqueous $Me_4NNO_3$ (I = 0.10 mol $dm^{-3}$)

| Parameter | log K | | | | |
|---|---|---|---|---|---|
| | TTDA | TTRA | TTEA | DTPA-BMA | DTPA |
| log $K_{CaL'}$(pH 7.4) | 9.72 | 8.56 | 8.13 | 5.11 | 6.43 |
| [ZnL]/[Zn][L] | 18.59 | 19.37 | 19.91 | 12.13 | 18.70 |
| [ZnHL]/[ZnL][H] | 7.41 | 4.15 | 4.7 | 4.04 | 5.60 |
| log $K_{ZnL'}$(pH 7.4) | 13.86 | 14.41 | 14.56 | 10.02 | 14.38 |
| [CuL]/[Cu][L] | 19.31 | 17.92 | 17.33 | 13.17 | 21.38 |
| [CuL]/[CuL][H] | 5.52 | 8.68 | 9.5 | 3.36 | 4.81 |
| log $K_{CuL'}$(pH 7.4) | 14.58 | 12.96 | 11.97 | 11.06 | 17.06 |

The stability constants of TTRA with $Gd^{3+}$, $Ca^{2+}$, $Zn^{2+}$, and $Cu^{2+}$ are in the order $[Zn(TTRA)]^{3-}$ (19.37)>[Cu(TTRA)]$^{3-}$ (17.92)>[Gd(TTRA)]$^{3-}$ (15.89)>[Ca(TTRA)]$^{3-}$ (13.52). For $Gd^{3+}$, TTRA complex has a smaller stability constant than TTDA complex. The stability constants of TTEA with $Ca^{2+}$, $Zn^{2+}$, and $Cu^{2+}$ are 13.48, 19.91, and 17.33 respectively. The stability of TTEA with $Gd^{3+}$ can not be determined by potentiometric titration. This is because the f orbital of $Gd^{3+}$ is ball-shaped, and the bonding between $Gd^{3+}$ and the ligand is totally provided by electrostatic interaction. In TTEA, the carbon number among three amino groups is 3 and 4 respectively; therefore, TTEA is very difficult to complex with metal ions. However, both of TTDA and TTRA, which have eight binding sites (three amino groups and five carboxyl groups), can complex with $Gd^{3+}$. The stability constants $logK_{GdL}$ of TTDA and TTRA are 22.77 and 15.89 respectively, indicating that the stability constant is related to the binding angle. However, for $Ca^{2+}$, $Zn^{2+}$, and $Cu^{2+}$, the influence is less because of the d orbital.

In addition, comparing TTDA, DTPA-BMA and DTPA, it can be found that the thermodynamic stability constants of complexes with the same metal ion is related to the basicity of the ligand. The more basic the ligand, the larger stability constant the metal complex. The thermodynamic stability constant for the same metal ion is in the order [M(TTDA)]=[M(DTPA)]>[M(DTPA-BMA)] ($M^{n+}=Gd^{3+}$, $Zn^{2+}$, $Ca^{2+}$, and $Cu^{2+}$. The reason is because the ionic bonding between the metal ion and the carboxyl groups of the ligand is stronger than the ionic-dipolar interaction between the metal ion and the amide groups of the ligand.

The thermodynamic stability constants of complexes with the same ligand is in the order GdL>CuL>ZnL>CaL, which is mainly related to the charge density. The ion radii of $Gd^{3+}$, $Zn^{2+}$, $Ca^{2+}$, and $Cu^{2+}$ is 1.22 Å (CN=8), 0.88 Å (CN=6), 1.26 Å (CN=8), and 0.87 Å (CN=6) respectively. It can be found that when the metal ion has a greater charge density, the metal complex formed has a larger thermodynamic stability constant.

Figure 5:
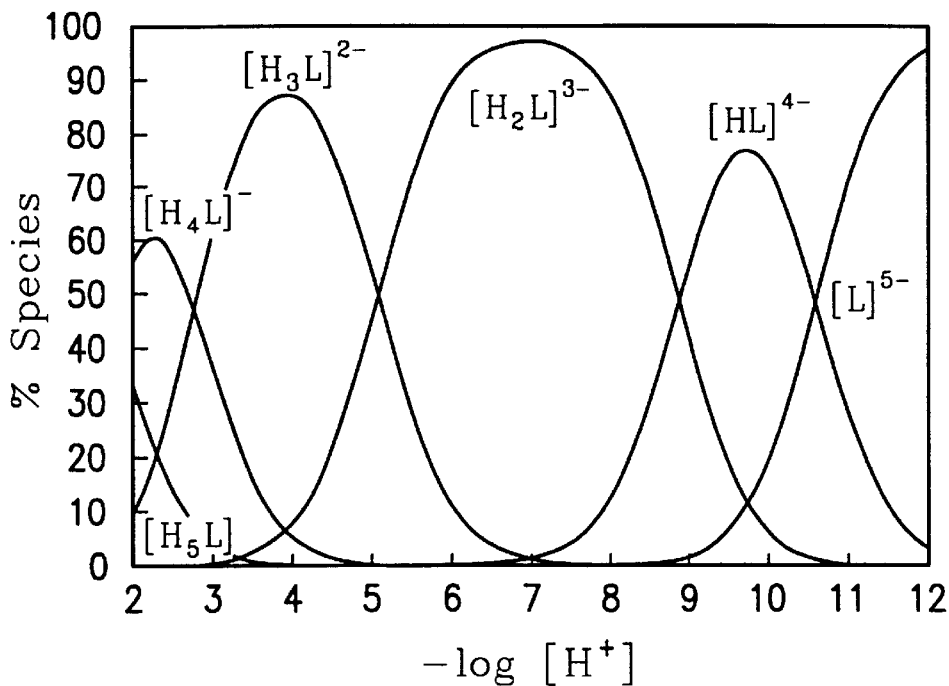
FIG. 5 shows the species distribution curves for a 7.0× $10^{-3}$ mol $dm^{-3}$ TTDA system at various pH values.

The protonated species distribution of TTDA, TTRA, and TTEA is shown in FIG. 5 to FIG. 9. In FIG. 5 shows that in the pH 5–9 range, the dominant species of TTDA ligand is the second protonated species $[H_2L]^{3-}$. When pH=7.0, the concentration of $[H_2L]^{3-}$ is the maximum (97.5%). In the pH 3–5 range, the dominant species is the third protonated species $[H_3L]^{2-}$. When pH=3.7, the concentration of $[H_3L]^{2-}$ is the maximum (87.75%). In the pH 9–10.5 range, the dominant species is the first protonated species $[HL]^{4-}$. When pH=9.8, the concentration of $[HL]^{4-}$ is the maximum (77.5%). In the pH 2–3 range, the dominant species is the fourth protonated species $[H_4L]^{-}$. When pH=2.3, the concentration of $[H_4L]^{-}$ is the maximum (60.9%). In the pH range greater than 11, the dominant species is the deprotonated species $[L]^{5-}$.

Figure 6:
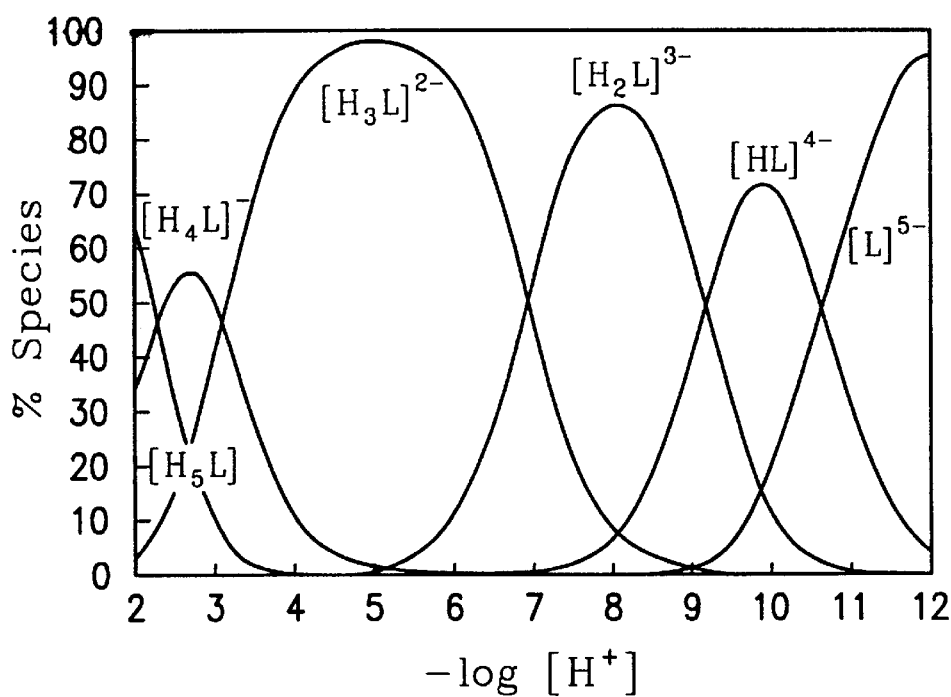
FIG. 6 shows the species distribution curves for a 7.0× $10^{-3}$ mol $dm^{-3}$ TTRA system at various pH values.

In FIG. 6 shows that in the pH 2–3.5 range, the dominant species of TTRA ligand is the fourth protonated species $[H_4L]^{-}$. When pH=2.7, the concentration of $[H_4L]^{-}$ is the maximum (55.9%). In the pH 3.5–7 range, the dominant species is the third protonated species $[H_3L]^{2-}$. When pH=5, the concentration of $[H_3L]^{2-}$ is the maximum (97.7%). In the pH 7–9 range, the dominant species is the second protonated species $[H_2L]^{3-}$. When pH=8.1, the concentration of $[H_2L]^{3-}$ is the maximum (86.5%). In the pH 9.5–10.5 range, the dominant species is the first protonated species $[HL]^{4-}$. When pH=9.9, the concentration of $[HL]^{4-}$ is the maximum (71.6%). In the pH range greater than 12, the dominant species is the deprotonated species $[L]^{5-}$. In the pH range less than 2, the dominant species is the totally protonated species $[H_5L]$.

Figure 7:
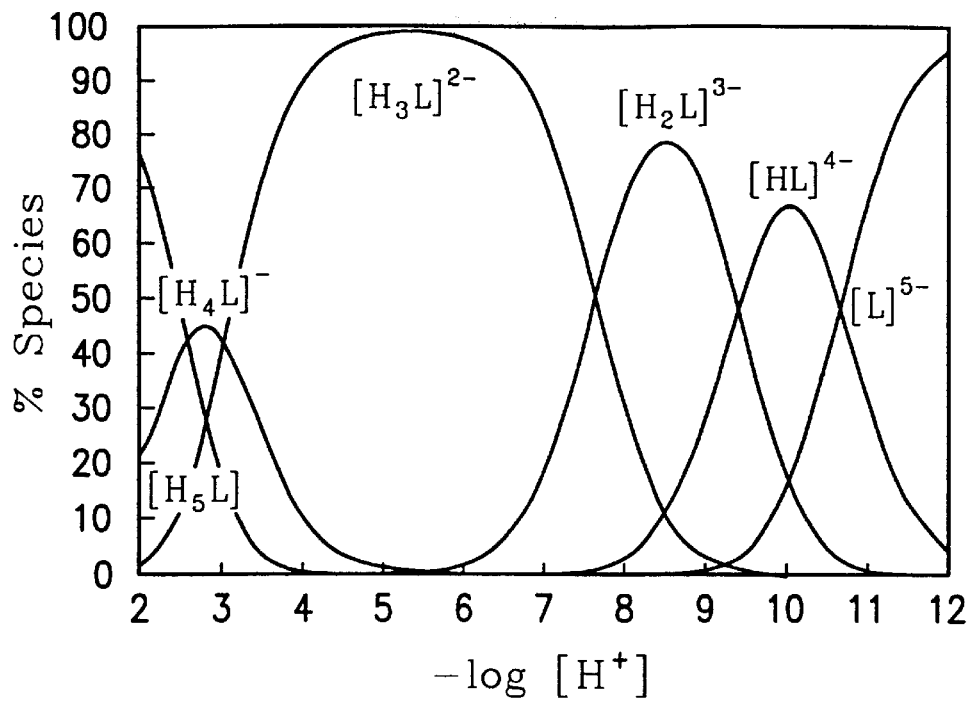
FIG. 7 shows the species distribution curves for a 7.0× $10^{-3}$ mol $dm^{-3}$ TTEA system at various pH values.

In FIG. 7 shows that in the pH 2.5–3.5 range, the dominant species of TTEA ligand is the fourth protonated species $[H_4L]^{-}$. When pH=2.8, the concentration of $[H_4L]^{-}$ is the maximum (45.9%). In the pH 3.5–7.5 range, the dominant species is the third protonated species $[H_3L]^{2-}$. When pH=5.2, the concentration of $[H_3L]^{2-}$ is the maximum (99.0%). In the pH 8–9.5 range, the dominant species is the second protonated species $[H_2L]^{3-}$. When pH=8.6, the concentration of $[H_2L]^{3-}$ is the maximum (78.8%). In the pH 9.5–11 range, the dominant species is the first protonated species $[HL]^{4-}$. When pH=10.1, the concentration of $[HL]^{4-}$ is the maximum (67.2%). In the pH range greater than 12, the dominant species is the deprotonated species $[L]^{5-}$. In the pH range less than 2, the dominant species is the totally protonated species $[H_5L]$.

Figure 8:
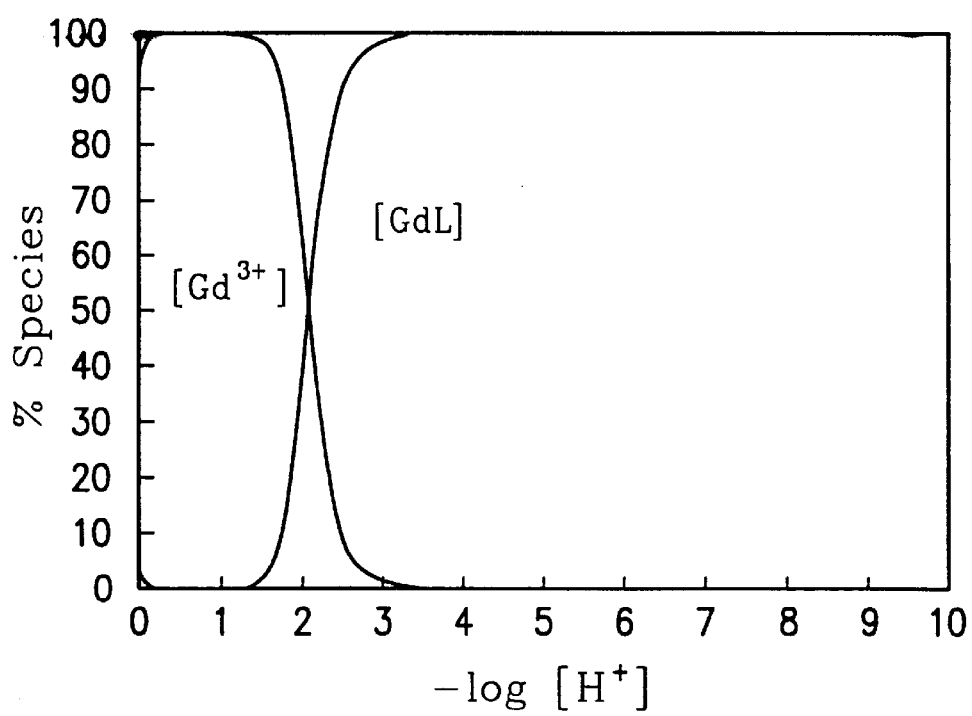
FIG. 8 shows the species distribution curves for a 7.0× $10^{-3}$ mol $dm^{-3}$ $[Gd(TTDA)]^{2-}$ system at various pH values.
Figure 9:
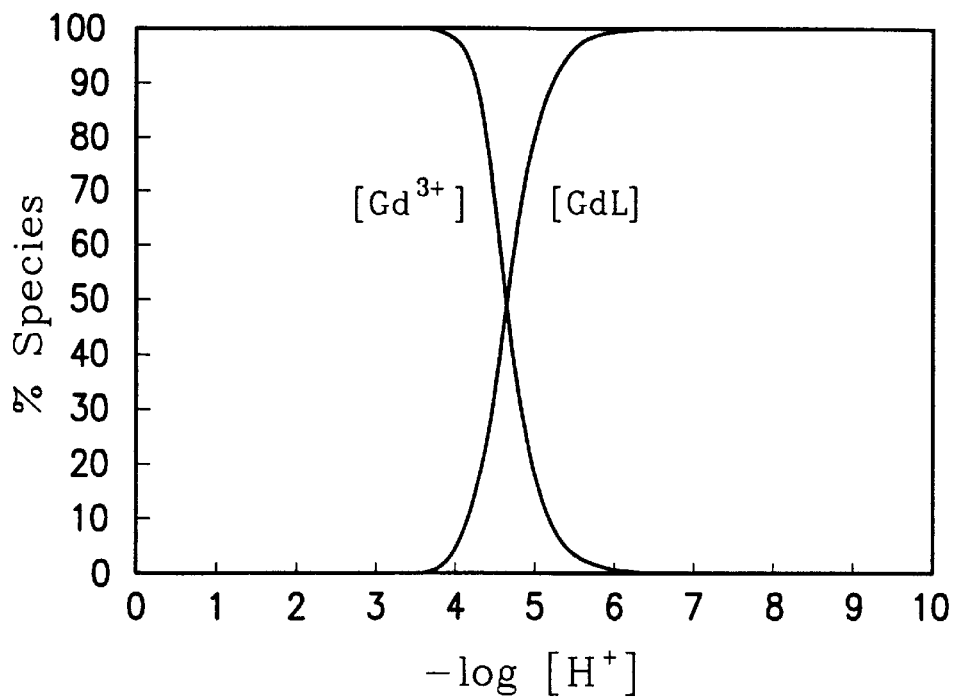
FIG. 9 shows the species distribution curves for a [Gd (TTRA)]$^{2-}$ system at various pH values.

The species distribution of the TTDA-$Gd^{3+}$ complex is shown in FIG. 8. It can be seen that below pH 1.5, the solution is present in the form of free $Gd^{3+}$ ion, and above pH 3.9, the solution is present in the form of metal complex. The maximum concentration is 99.7%. The species distribution of the TTRA-$Gd^{3+}$ complex is shown in FIG. 9. It can be seen that below pH 4.0, the solution is present in the form of free $Gd^{3+}$ ion, and above pH 6, the solution is present in the form of metal complex. At pH 6.5, the maximum concentration is 98%.

3. Conditional Stability Constants:

To understand the stability of the metal complex in vivo, the conditional stability constant is more important than the thermodynamic stability constant. The conditional stability constant is the stability constant of a metal complex under physiological conditions (pH 7.4).

The reaction of forming a metal complex from a metal ion and an organic ligand can be depicted as follows:

$$M + L \leftrightarrows ML \qquad (1)$$

M: metal ion, L: organic ligand, ML: metal complex The conditional stability constant is defined by equation (2):

$$K_{cond} = \frac{[ML]}{[M]}\{[L] + [HL] + [H_2L] + \ldots\}^{-1} \qquad (2)$$

The relationship between the conditional stability constant and the thermodynamic stability constant is defined by equation (3):

$$K_{cond} = K_{therm} \frac{[L]}{[L_T]} \quad (3)$$

$L_T$ is the concentration of the uncomplexed organic ligand, which is expressed by equation (4):

$$L_T = \{[L] + [HL] + [H_2L] + \ldots\} \quad (4)$$

Substituting equation (4) into equation (3):

$$K_{cond} = K_{therm}\{1 + K_1^H[H^+] + K_1^H K_2^H[H^+]^2 + \ldots\}^{-1} = K_{therm} \alpha_H \quad (5)$$

wherein $\alpha_H = \{1 + K_1^H[H^+] + K_1^H K_2^H[H^+]^2 + \ldots\}^{-1}$

Figure 10:
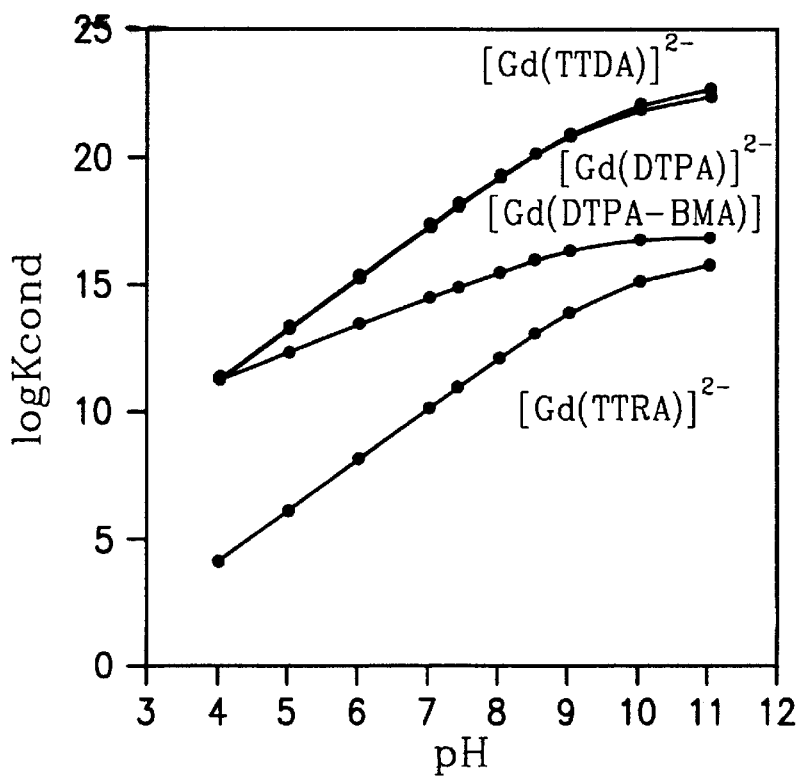
FIG. 10 shows the pH dependence of the conditional stability constant for the gadolinium complexes.

The conditional stability constant of [Gd(TTDA)]$^{2-}$ and [Gd(TTRA)]$^{2-}$ at various pH levels can be calculated by formula (5) The results are shown in Table 2. The stability constant under physiological conditions (pH 7.4) is in the order [Gd(TTDA)]$^{2-}$ (22.77)=[Gd(DTPA)]$^{2-}$ (22.46)>[Gd(DTPA-BMA)] (16.95)>[Gd(TTRA)]$^{2-}$ (15.89). FIG. 10 shows the pH dependence of the conditional stability constant for the gadolinium complexes. At high pH (pH>11.0), the organic ligand is totally deprotonated, and the conditional stability constant of the metal complex is the thermodynamic stability constant. At pH 11.0, the stability constants (log $K_{ML}$) of [Gd(TTDA)]$^{2-}$ and [Gd(DTPA)]$^{2-}$ are larger than that of [Gd(DTPA-BMA)] by 5.8 and 5.5 respectively. At pH 7.4, the stability constants of [Gd(TTDA)]$^{2-}$ and [Gd(DTPA)]$^{2-}$ are larger than that of [Gd(DTPA-BMA)] by 3.3 and 3.2 respectively. At pH 4.0, the thermodynamic stability constants and the conditional stability constants of [Gd(TTDA)]$^{2-}$, [Gd(DTPA)]$^{2-}$, and [Gd(DTPA-BMA)] are all the same (11.25). At pH 11, the conditional stability constant of [Gd(TTRA)]$^{2-}$ is 15.89 and is decreased to 1.14 at pH 4.0. The results show that the conditional stability constant (log $K_{cond}$) of the gadolinium complex is very related to the basicity of the organic ligand. TTDA and DTPA have close basicity, and their conditional stability constants are similar. However, at pH=4.0, since [Gd(TTRA)]$^{2-}$ has very large basicity, its conditional stability constant is only 4.14, which is much lower than those of [Gd(TTDA)]$^{2-}$, [Gd(DTPA)]$^{2-}$ and [Gd(DTPA-BMA)].

4. The Selectivity Constants:

The toxicity of the MRI contrast agent is mainly due to the free metal ion (such as free Gd$^{3+}$) from the dissociation of the MRI contrast agent. Metal ions such as Zn$^{2+}$, Ca$^{2+}$, and Cu$^{2+}$ in the animal body compete with Gd$^{3+}$ in the gadolinium complex, thus free Gd$^{3+}$ is formed. The free Gd$^{3+}$ will bind to the ligand in the body, such as amino acid, citric acid, or serum protein, to form complex, thus causing physiological unequivalence.

Among Zn$^{2+}$, Ca$^{2+}$, and Cu$^{2+}$, Zn$^{2+}$ is the main cause of the dissociation of the gadolinium complex in the animal body. That is because the Zn$^{2+}$ concentration in plasma is very high (10–50 μM). Zn$^{2+}$ can bind to a large amount of ligand to form a stable complex; thus, a large amount of Gd$^{3+}$ is formed. As to the other metal ions in the animal body, Cu$^{2+}$ concentration in plasma is only 1–10 μm. Although Ca$^{2+}$ concentration in plasma is very high (2.5–4 mM), the Ca$^{2+}$ complexes with TTDA, DTPA, and DPTA-BMA have a low stability constant; thus, gadolinium complex will not be dissociated to form free gadolinium ion. In addition, as to Fe$^{3+}$, the bonding of Fe$^{3+}$ and the ligand for ferritin and hemosiderin is very strong; thus, replacement reaction with the gadolinium complex will not occur.

The selectivity constant of the ligand for Gd$^{3+}$ over M$^+$ is defined as log K(Gd$^{3+}$/M$^{n+}$) (M$^{n+}$=Zn$^{2+}$, Ca$^{2+}$, and Cu$^{2+}$). Table 3 shows the selectivity constants of [Gd(TTDA)]$^{2-}$, [Gd(TTRA)]$^{2-}$, [Gd(DTPA-BMA)], and [Gd(DTPA)]$^{2-}$ over Zn$^{2+}$, Ca$^{2+}$, and Cu$^{2+}$. It is found that the selectivity constant of [Gd(TTDA)]$^{2-}$ over Zn$^{2+}$ is similar to that of [Gd(DTPA-BMA)], which is higher than that of [Gd(DTPA)]$^{2-}$, indicating that TTDA shows more favorable selectivity toward Gd$^{3+}$ over Zn$^{2+}$ than DTPA.

5. Modified Selectivity Constants:

Taking the thermodynamic stability constant of the gadolinium complex and the stability constant of the ligand with Zn$^{2+}$, Ca$^{2+}$, and Cu$^{2+}$ into consideration, a modified selectivity constant can be obtained, which is expressed by $K_{sel}'$ and calculated by the equation (6):

$$K_{sel}' = K_{therm}(\alpha_H^{-1} + \alpha_{CaL}^{-1} + \alpha_{CuL}^{-1} + \alpha_{ZnL}^{-1})^{-1} \quad (6)$$

wherein $$\alpha_H^{-1} = 1 + K_1^H[H^+] + K_1^H K_2^H[H^+]^2 + \quad (7)$$

$$\alpha_{CaL}^{-1} = 1 + K_{CaL}[Ca^{2+}] \quad (8)$$

$$\alpha_{CuL}^{-1} = 1 + K_{CuL}[Cu^{2+}] \quad (9)$$

$$\alpha_{ZnL}^{-1} = 1 + K_{ZnL}[Zn^{2+}] \quad (10)$$

Knowing that the concentration of Ca$^{2+}$, Cu$^{2+}$, and Zn$^{2+}$ in plasma is 2,5 mM, 1 μm, and 50 μm and the stability constant of the metal complex, the log $K_{sel}'$ of the gadolinium complex at pH 7.4 can be calculated. The results are shown in Table 3. The modified selectivity constant is in the order [Gd(DTPA-BMA)] (9.03)>[Gd(TTDA)]$^{2-}$ (8.44)>[Gd(DTPA)]$^{2-}$ (7.07)>[Gd(TTRA)]$^{2-}$ (2.64). In addition, it is known that LD$_{50}$ of [Gd(DTPA-BMA)] is 14.8 mmol/kg and that of [Gd(DTPA)]$^{2-}$ is 5.6 mmol/kg, it can be concluded that the toxicity of the linear gadolinium complex is not related to the thermodynamic stability constant, but related to the selectivity stability constant. Therefore, it can be predicted that LD$_{50}$ of [Gd(TTDA)]$^{2-}$ may be higher than that of [Gd(DTPA)]$^{2-}$ and the acute toxicity is lower.

TABLE 3

The selectivity of [Gd(TTDA)]$^{2-}$, [Gd(TTRA)]$^{2-}$, [Gd(DTPA-BMA)] and [Gd(DTPA)]$^{2-}$ over Zn$^{2+}$, Ca$^{2+}$, and Cu$^{2+}$.

| Parameter | TTDA | TTRA | DTPA-BMA | DTPA |
|---|---|---|---|---|
| log K(Gd/Zn) | 4.18 | — | 4.82 | 3.76 |
| log K(Gd/Cu) | 3.46 | — | 3.78 | 1.08 |
| log K(Gd/Ca) | 8.32 | 2.37 | 9.73 | 11.71 |
| log K sel' | 8.44 | 2.64 | 9.03 | 7.07 |

The stability of the metal complex in the animal body is very important for MRI contrast agent, and pM value is one of the important data. The pM value is defined as $-\log M^{n+}]_{free}$ at pH 7.4 can be calculated by equation (11)

$$pM = \frac{\alpha_L \cdot T_M}{\alpha_{ML} K_{ML}(T_L - T_M)} \quad (11)$$

wherein $$\alpha_L = 1 + \beta_n^H[H^{+n}] = 1 + K_1^H[H^+] + K_1^H K_2^H[H^+]^2 + \quad (12)$$

$$\alpha_{ML} = 1 + \beta_{MH_nL}^H[H^+]^n = 1 + K_{MHL}[H^+] + K_{MH_2L}[H^+]^2 + \quad (13)$$

$T_L$ represents the total concentration of the ligand, and $T_M$ the total concentration of the metal ion. In the examples, $T_L$ is $1.1 \times 10^{-5}$ mol dm$^{-3}$ and $T_M$ is $1.0 \times 10^{-6}$ mol dm$^{-3}$. Thus, pM of the metal complex at pH 7.4 can be calculated, and the results are shown in Table 4. It can be seen that the pM values of [M(DTPA)] and [M(TTDA)] are higher than that of [M(DTPA-BMA)] (M=$Gd^{3+}$, $Ca^{2+}$, $Zn^{2+}$, and $Cu^{2+}$). The reason is that the basicities of DTPA and TTDA are stronger than that of DTPA-BMA; therefore, the DTPA and TTDA complexes with the metal are more stable and the complexes will not be dissociated to form free metal ions. The pM value is related to the stability constant of the metal complex. That is to say, the larger the stability constant of the metal complex, the smaller the free metal ion concentration.

various gadolinium complexes are similar. In addition, it is also found that in the pH range 3–10, the average relaxivities for $[Gd(TTDA)]^{2-}$ and [Gd(DTPA-BMA)] are 4.10 and 4.05 $dm^{-3}$ $mmol^{-1}s^{-1}$, which are similar too. It is found that [Gd(DTPA-BMA)] contains one inner-sphere water molecule by the X-ray single crystal analysis, and $[Dy(TTDA)]^{2-}$ also contains one inner-sphere water molecule by the $^{17}$O-NMR analysis. Since the $[Gd(TTDA)]^{2-}$ has the similar structure to $[Dy(TTDA)]^{2-}$, it can be deduced that $[Gd(TTDA)]^{2-}$ contains one inner-sphere water molecule. That is why the $R_1$ of $[Gd(TTDA)]^{2-}$ is similar to those of $[Gd(DTPA)]^{2-}$ and [Gd(DTPA-BMA)].

TABLE 4

|  | TTDA $logK_{ML}$ | pM | TTRA $logK_{ML}$ | pM | TTEA $logK_{ML}$ | pM | DTPA-BMA $logK_{ML}$ | pM | DTPA $logK_{ML}$ | pM |
|---|---|---|---|---|---|---|---|---|---|---|
| $Gd^{3+}$ | 22.77 | 17.03 | 15.89 | 9.80 | — | — | 16.95(6) | 13.68 | 22.46 | 17.14 |
| $Ca^{2+}$ | 15.45 | 9.73 | 13.52 | 8.20 | 13.48 | 7.64 | 7.72(7) | 3.95 | 10.75 | 5.45 |
| $Zn^{2+}$ | 18.95 | 13.22 | 19.37 | 13.67 | 19.91 | 13.08 | 12.13(4) | 8.86 | 18.70 | 13.39 |
| $Cu^{2+}$ | 19.31 | 13.58 | 17.92 | 13.12 | 17.33 | 12.63 | 13.17(2) | 9.90 | 21.38 | 16.06 |

6. Inner-sphere Water Molecules:

The chemical shift (d.i.s.) of the Dy(III)-induced $^{17}$O is determined by $^{17}$O-NMR. The relationship between the Dy(III) complex concentration and d.i.s. is shown in equation (14)

$$d.i.s.=q\Delta[Dy(ligand)_n](H_2O)_q/[H_2O] \qquad (14)$$

Figure 11:
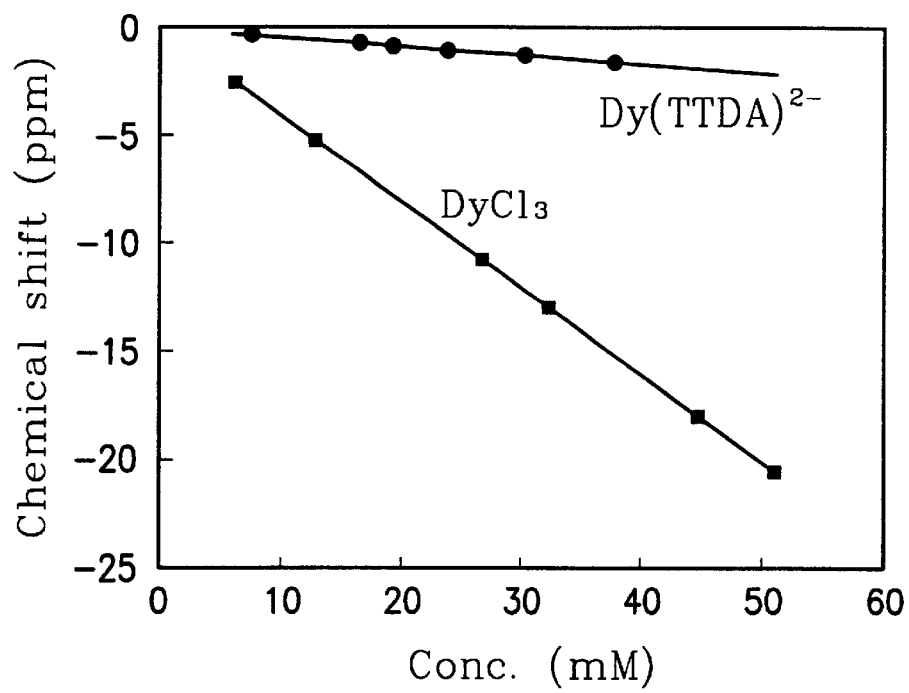
FIG. 11 shows the Dy(III)-induced $H_2O$ $^{17}O$-NMR chemical shift versus complex concentration for $Dy(TTDA)^{2-}$ and $DyCl_3$ solutions.

The slope of equation (14) is $q\Delta/[H_2O]$, and q refers to the inner-sphere water molecule. In FIG. 11, the slope for $[Dy(TTDA)]^{2-}$ is −48.8, and that for $DyCl_3$ is −445.6. It is known that Dy(III) can bind with eight water molecules at low concentration, and q is in a linear relationship with the slope. Thus, it can be calculated that q is 0.90 for $[Dy(TTDA)]^{2-}$; that is to say, $[Dy(TTDA)]^{2-}$ contains one inner-sphere water molecule. In the same manner, the q values for $[Dy(DTPA)]^{2-}$, $[Dy(DOTA)]^-$, and $[Dy(EDTA)]^-$ are 1.3, 0.8, and 2.3 respectively. This indicates that the inner-sphere water molecules for $[Dy(DTPA)]^{2-}$ and $[Dy(DOTA)]^-$ are only one, which is less than that for $[Dy(EDTA)]^-$ (2–3 inner-sphere water molecules).

Figure 12:
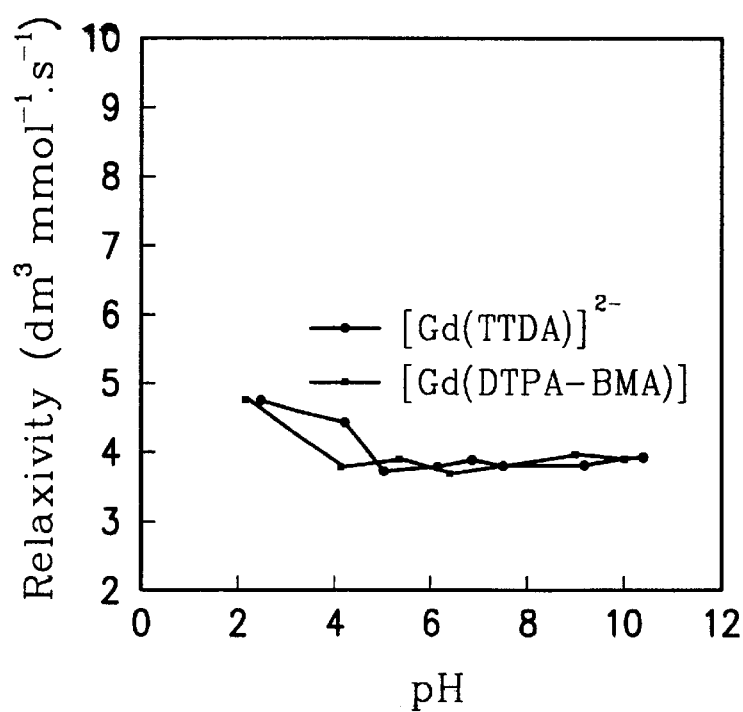
FIG. 12 shows pH dependence of the relaxivity for the complexes [Gd(TTDA)]$^{2-}$ and [Gd(DTPA-BMA)].

7. The Effect of pH Value on Relaxivity:

The relaxivities $R_1$ for the complexes $[Gd(TTDA)]^{2-}$ and [Gd(DTPA-BMA)] at various pH values are given in FIG. 12. The relaxivity curve exhibits no pH dependence over the range 4–10. Therefore, no ligand dissociation occurred with this pH range and the hydration number remains constant. However, in the pH range less than 4.0, $R_1$ increase with the decrease of pH. The reason is that the oxygen atoms on the carboxyl groups may be partially protonated, thus the carboxyl groups can not coordinate with the gadolinium ion. This increases the inner-sphere water molecules on the gadolinium ion, and the $R_1$ increases.

The relaxivities ($R_1$) of various gadolinium complexes at various pH are shown in Table 5. It can be found that at pH=6.75, the $R^1$ of $[Gd(TTDA)]^{2-}$ is 3.85; at pH=7.5, the $R_1$ of $[Gd(DTPA)]^{2-}$ is 3.71; and at pH=6.3, the $R^1$ of [Gd(DTPA-BMA)] is 3.74. It can be concluded that the $R_1$ for

TABLE 5

| Complex | pH | Relaxivity $R_1$/ $dm^3$ $mmol^{-1}s^{-1}$ |
|---|---|---|
| $[Gd(DTPA)]^{2-}$ | 7.5 ± 0.1 | 3.71 ± 0.05 |
| [Gd(DTPA-BMA)] | 6.3 ± 0.1 | 3.74 ± 0.05 |
| $[Gd(TTDA)]^{2-}$ | 6.7 ± 0.1 | 3.85 ± 0.03 |

Study on Imaging for the Animals 1-1. Materials and Methods:

Sodium pentobarbital was injected into the tail veins of 250–350 mg rats (which have a healthy liver or tumorous liver) in a dosage of 40–50 mg/kg. The rats were placed on the head coil of an 1.5 T magnetic resonance imaging instrument. The T1-weighted (TR/Te, 15/6.1 msec) image was obtained by turbo field echo with the number of signal average. The field of view (FOV), the cross-sectional thickness, and the image matrix were 22 cm, 4 mm, and 128×256 respectively.

Before injecting the contrast agent, a set of T1-weighted baseline images were taken. In the first five minutes, the images were taken at a very short time interval in order to evaluate the dynamic enhancement condition. Afterwards, the images were taken every 10, 20, 30, 40, 50, and 60 minutes in order to observe the continuous enhancement effect.

1-2. Image Analysis:

By means of the computer software contained in the MRI instrument, the region of interest (ROI) can be determined by the operator. The signal intensities (SI) of liver, phantom, and kidney were measured. The enhancement percentage of an organ (liver or kidney) and the enhancement percentage of liver relative to kidney were calculated by the following equations. The statistical method used was Wilcoxon Signed Rank Test.

$$Enhancement\ percentage = \frac{SI_{post}/SI_{phantom(post)} - SI_{pre}/SI_{phantom(pre)}}{SI_{pre}/SI_{phantom(pre)}}$$

-continued $SI_{post}$: SI of an organ after injecting the contrast agent $SI_{pre}$: SI of an organ before injecting the contrast agent $SI_{phantom(post)}$: SI of phantom after injection the contrast agent $SI_{phantom(pre)}$: SI of phantom before injection the contrast agent Contrast Enhancement percentage of liver relative to kidney =

$$\frac{(SI_{liver})_T}{(SI_{kidney})_T}$$

$SI_{kidney}$: SI of kidney $SI_{liver}$: SI of liver

T: injection time

Figure 13:
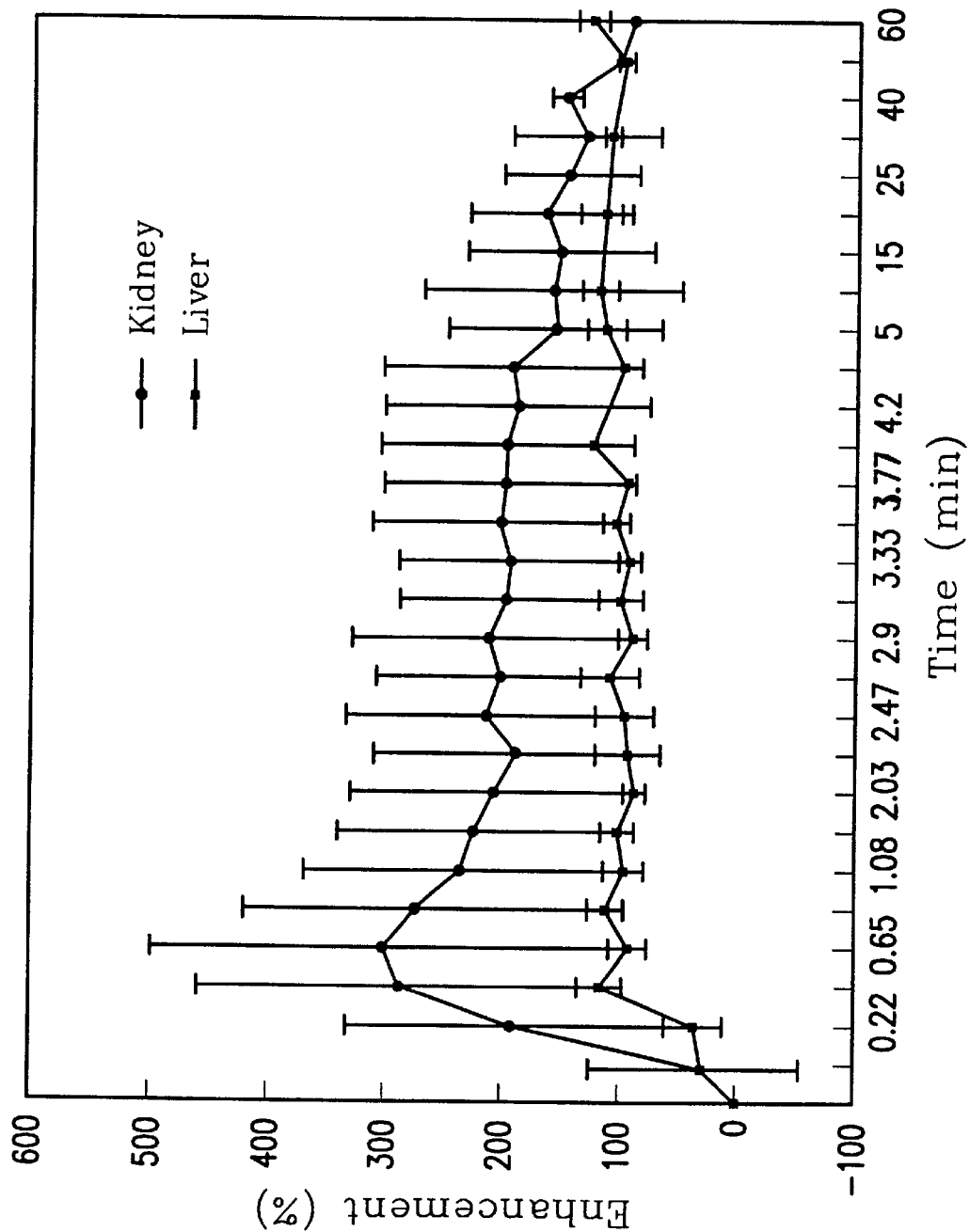
FIG. 13 shows the enhancement(%) of liver and kidney after injecting 0.1 mmol/kg of [Gd(TTDA)]$^{2-}$ versus time.
Figure 14:
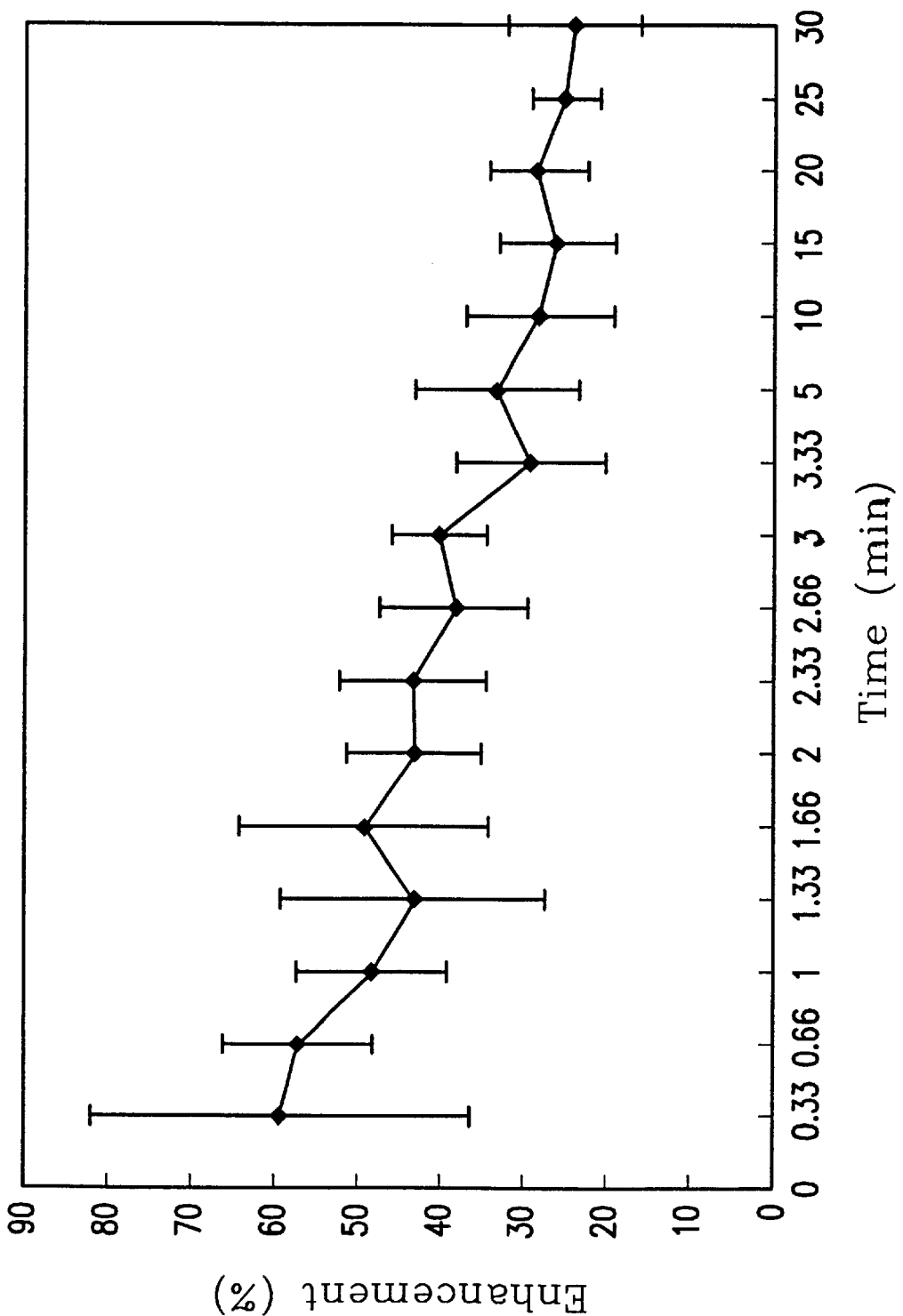
FIG. 14 shows the enhancement(%) of liver after injecting 0.1 mmol/kg of [Gd(DTPA)]$^{2-}$ versus time.
Figure 15:
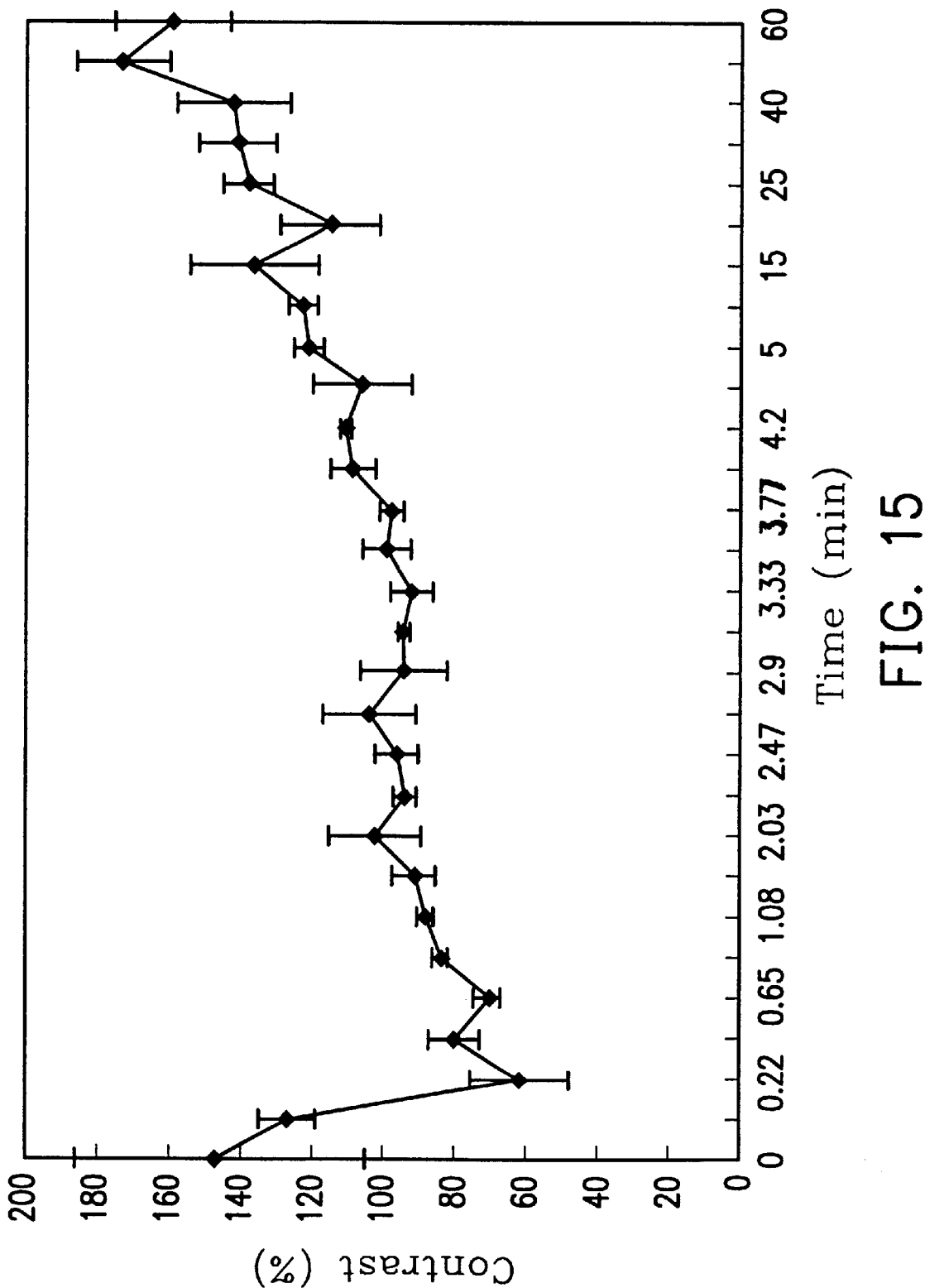
FIG. 15 shows the contrast enhancement(%) of liver relative to kidney after injecting 0.1 mmol/kg of [(Gd (TTDA))]$^{2-}$ versus time.

2. Results and Discussions of Magnetic Resonance Imaging:

FIG. 13 shows the enhancement(%) of liver and kidney of a healthy rat after injecting 0.1 mmol/kg of [Gd(TTDA)]$^{2-}$ versus time. FIG. 14 shows the enhancement(%) of liver of a healthy rat after injecting 0.1 mmol/kg of [Gd(DTPA)]$^{2-}$ (Magnevist, a commercial MRI contrast agent) versus time. FIG. 15 shows the contrast enhancement(%) of liver relative to kidney of a healthy rat after injecting 0.1 mmol/kg of [Gd(TTDA)]$^{2-}$ versus time.

Figure 16:
FIG. 16 shows the coronal cross-sectional image T1WI/TFE(TR/TE 15/6.1 msec, Flip25°) of the healthy rat at the ureter (A) before injecting, (B) 3 minutes after injecting, (C) 30 minutes after injecting, and (D) 50 minutes after injecting 0.1 mmol/kg of [Gd(TTDA)]$^{2-}$, The arrow indicates the location of the ureter.
Figure 16:
Figure 16:
Figure 16:

As to the [Gd(TTDA)]$^{2-}$ injection, from FIG. 13, it can be seen that after the [Gd(TTDA)]$^{2-}$ injection, the liver enhancement increases rapidly and reaches 116±17% the maximum within 1 minute after injection, and remains the maximum afterwards until 60 minutes after injection. The kidney enhancement reaches 300±100% the maximum within 1 minute after injection, and then decreases gradually. At 60 minutes after injection, the kidney enhancement decreases to 76±8%. From FIG. 15, it can be seen that the contrast enhancement of liver relative to kidney first decreases and then increases. It is 1.47±0.45 before the enhancement, decreases to 0.71±0.04 within 1 minute after injection, increases to 1 within 5 minutes, and increases to 1.59±0.16 60 minutes after injection. FIG. 16 shows the coronal cross-sectional ureter image of of the healthy rat after injecting 0.1 mmol/kg of [Gd(TTDA)]$^{2-}$. It can be seen that 3 minutes after injection (FIG. 16(B)), the ureter image is enhanced.

Figure 17:
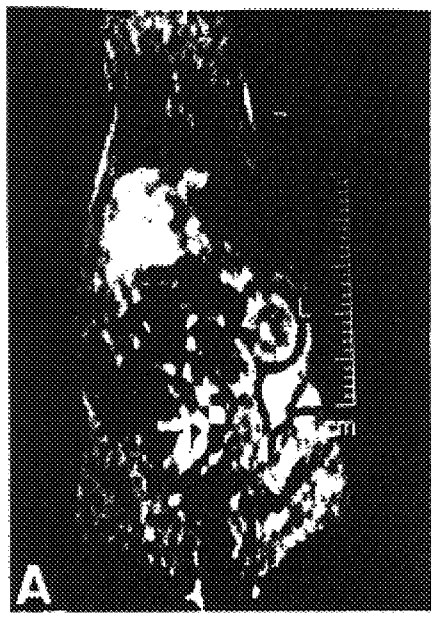
FIG. 17 shows the coronal cross-sectional image T1WI/TFE(TR/TE 15/6.1 msec, Flip25°) of the healthy rat at the kidney (A) before injecting, (B) 1 minute after injecting, (C) 10 minutes after injecting, and (D) 30 minutes after injecting 0.1 mmol/kg of [Gd(DTPA)]$^{2-}$, The arrow indicates the location of the ureter.
Figure 17:
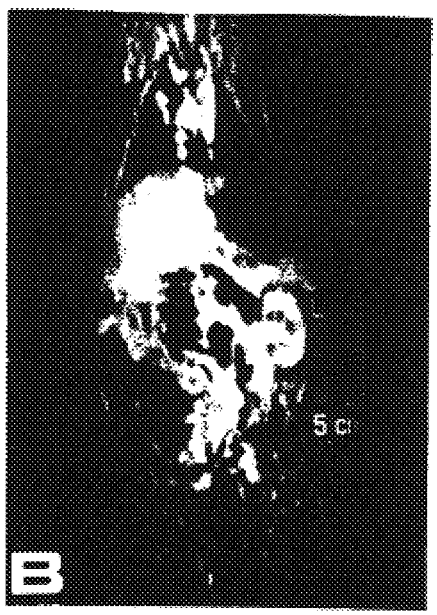
Figure 17:
Figure 17:

As to the [Gd(DTPA)]$^{2-}$(commercial MRI contrast agent) injection, from FIG. 14, it can be seen that after injecting 0.1 mmol/kg of [Gd(DTPA)]$^{2-}$, the liver enhancement reaches 57±9% the maximum within 1 minute and then decreases to 24±7% after 30 minutes. FIG. 17 shows the coronal cross-sectional kidney image of the healthy rat after injecting 0.1 mmol/kg of [Gd(DTPA)]$^{2-}$. It can be seen that the kideny enhancement reaches the maximum at 1 minute after injection and then decreases gradually. At 30 minutes after injection, the enhancement decreases to 109±14%. From the results of the [Gd(TTDA)]$^{2-}$ and [Gd(DTPA)]$^{2-}$ injection, it can be concluded that [Gd(TTDA)]$^{2-}$ can be rapidly expelled out of the rat body via the kidney and can provide higher liver enhancement effect compared to Gd(DTPA)]$^{2-}$.

Figure 18:
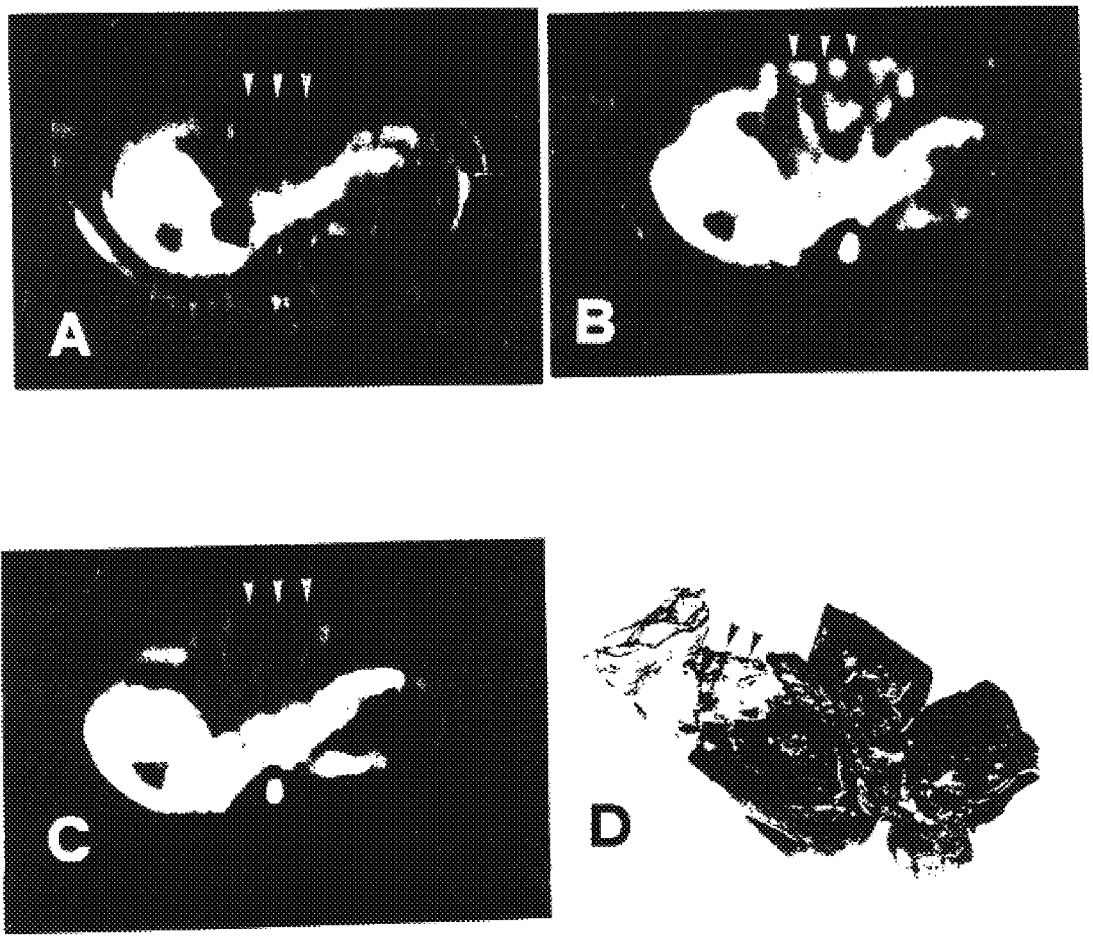
FIGS. 18(A)–18(C) shows the axial cross-sectional image T1WI/TFE(TR/TE 15/6.1 msec, Flip25°) of the tumorous liver of the rat (A) before injecting, (B) 10 minutes after injecting, and (C) 30 minutes after injecting after injecting 0.1 mmol/kg of [Gd(TTDA)]$^{2-}$.
FIG. 18(D) shows a liver sample. The arrows indicates the location of the tumorous liver.

FIG. 18 shows the axial cross-sectional image of the tumorous liver of the rat after injecting 0.1 mmol/kg of [Gd(TTDA)]$^{2-}$ versus time. It shows that the tumorous liver enhancement reaches 94±11% the maximum within 1 minute after injection, and the image remains the maximum enhancement for 30 minutes. However, the tumorous liver signal is still lower than the singal of the adjacent healthy liver, indicating that the tumorous liver is negative enhancement relative to the healthy liver.

In summary, after injecting 0.1 mmol/kg of [Gd(TTDA)]$^{2-}$ to the healthy rat, the kidney enhancement reaches the maximum within 1 minute and then gradually decreases. The ureter image is enhanced within 3 minutes after injection. This indicates that [Gd(TTDA)]$^{2-}$ can be rapidly expelled out of the rat body via the kidney. The healthy liver has continuous enhancement for 60 minutes, indicating that [Gd(TTDA)]$^{2-}$ has liver enhancement effect. The tumorous liver has continuous enhancement for 30 minutes, and the tumorous liver signal is lower than the signal of the adjacent healthy liver, indicating that the tumorous liver is negative enhancement relative to the healthy liver. Accordingly, [Gd(TTDA)]$^{2-}$ is a potential MRI contrast agent.

Conclusion

According to the above, the present invention discusses the protonation constants of three DTPA derivative ligands, TTDA, TTRA, and TTEA, the stability constants of the metal complexes formed from Gd, Zn, Ca, or Cu with the three ligands, the selectivity constants of the organic ligands for the gadolinium complex over the calcium, zinc, or copper ion, the conditional stability constants of the metal complexes under physiological conditions (pH 7.4), the modified selectivity constants of the metal complexes, and pM values of the dissociated metal ions. From the conditional stability constants, selectivity constants, and modified selectivity constants results, it can be seen that [Gd(TTDA)]$^{2-}$ has very high stability in the animal body. Finally, the relaxivities $R^1$ for the complex [Gd(TTDA)]$^{2-}$ at various pH values are also discussed. From the above thermodynamic parameters results, it can be found that although [Gd(TTDA)]$^{2-}$ is an ionic complex, its thermodynamic stability constant is very close to that of [Gd(DTPA)]$^{2-}$, a commerciallized MRI contrast agent. However, as to the selectivity constant and modified selectivity constant which are related to the toxicity (LD$_{50}$), the selectivity constants of TTDA over zinc and copper ions are higher than those of DTPA, and the modified selectivity constant of [Gd(TTDA)]$^{2-}$ (logK$_{sel}$'=8.44) is higher than that of [Gd(DTPA)]$^{2-}$ (logK$_{sel}$'=7.04) indicating that the acute toxicity of [Gd(TTDA)]$^{2-}$ may be lower than [Gd(DTPA)]$^{2-}$. In addition, the relaxivity of [Gd(TTDA)]$^{2-}$ (R$_1$=3.85 dm$^3$ mmol$^{-1}$ s$^{-1}$) is close to that of [Gd(DTPA)]$^{2-}$ (R$_1$=3.70 dm$^3$ mmol$^{-1}$ s$^{-1}$). Moreover, the magnetic resonance images also show good results. In conclusion, [Gd(TTDA)]$^{2-}$ could make a good MRI contrast agent.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A triaminepentaacetic acid compound represented by the following formula

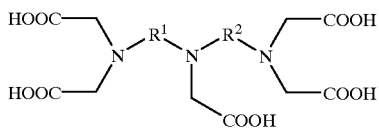

wherein
$R^1$ is $-(CH_2)_n-X-(CH_2)_n-$, wherein n=1 to 5, X is $-O-$ or $-S-$;
$R^2$ is $-(CH_2)_m-X-(CH_2)_m-$, wherein m=1 to 5, X is $-O-$ or $-S-$; and
$R^1$ and R2 can be the same or different.

2. A triaminepentaacetic acid compound represented by the following formula

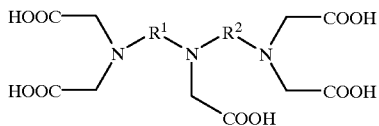

wherein
$R^1$ is $-(CH_2)_n-$, wherein n=1 to 5, X is $-O-$ or $-S-$;
$R^2$ is $-(CH_2)_m-X-(CH_2)_m-$, wherein m=1 to 5, X is $-O-$ or $-S-$; and
$R^1$ and R2 can be the same or different.

3. The compound as claimed in claim 2, wherein n=2.

4. A triaminepentaacetic acid compound represented by the following formula

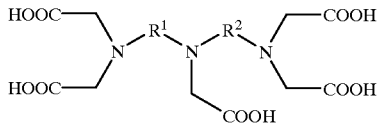

wherein
$R^1$ is $-(CH_2)_n-X-(CH_2)_n-$, wherein n=1–5, X is $-O-$ or $-S-$;
$R^2$ is $-(CH_2)_m-$, wherein m=1–5; and
$R^1$ and R2 can be the same or different.

5. The compound as claimed in claim 4, wherein m=3.

6. A paramagnetic metal complex represented by the formula ML,
wherein
M is a central metal ion, which is selected from the group consisting of ions of metals of Lanthanide series, manganese ion, iron ion, cobalt ion, copper ion, nickel ion, and chromium ion; and
L is an organic ligand which includes a compound represented by the following formula

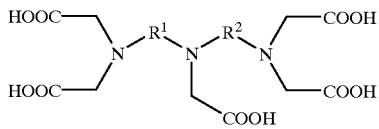

wherein
$R^1$ is $-(CH_2)_n-X-(CH_2)_n-$, wherein n=1–5, X is $-O-$ or $-S-$;
$R^2$ is $-(CH_2)_m-X-(CH_2)_m-$, wherein m=1–5, X is $-O-$ or $-S-$; and
$R^1$ and $R^2$ can be the same or different.

7. A paramagnetic metal complex represented by the formula ML,
wherein
M is a central metal ion, which is selected from the group consisting of ions of metals of Lanthanide series, manganese ion, iron ion, cobalt ion, copper ion, nickel ion, and chromium ion; and
L is an organic ligand which includes a compound represented by the following formula

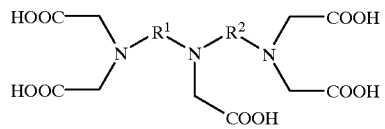

wherein
$R^1$ is $-(CH_2)_n-$, wherein n=1–5;
$R^2$ is $-(CH_2)_m-X-(CH_2)_m-$, wherein m=1–5, X is $-O-$ or $-S-$; and
$R^1$ and $R^2$ can be the same or different.

8. The metal complex as claimed in claim 7, wherein n=2.

9. A paramagnetic metal complex represented by the formula ML,
wherein
M is a central metal ion, which is selected from the group consisting of ions of metals of Lanthanide series, manganese ion, iron ion, cobalt ion, copper ion, nickel ion, and chromium ion; and
L is an organic ligand which includes a compound represented by the following formula

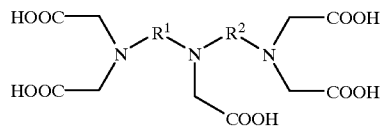

wherein
$R^1$ is $-(CH_2)_n-X-(CH_2)_n-$, wherein n=1–5, X is $-O-$ or $-S-$;
$R^2$ is $-(CH_2)_m-$, wherein m=1–5; and
$R^1$ and $R^2$ can be the same or different.

10. The metal complex as claimed in claim 9, wherein m=3.

11. The compound as claimed in claim 1, wherein n=2 to 4 and m=2–4.

12. The compound as claimed in claim 2, wherein n=2 to 4 and m=2–4.

13. The compound as claimed in claim 4, wherein n=2 to 4 and m=2–4.

14. The compound as claimed in claim 6, wherein n=2 to 4 and m=2–4.

15. The compound as claimed in claim 7, wherein n=2 to 4 and m=2–4.

16. The compound as claimed in claim 9, wherein n=2 to 4 and m=2–4.

* * * * *